United States Patent
Graichen et al.

(10) Patent No.: US 9,617,277 B2
(45) Date of Patent: *Apr. 11, 2017

(54) POLYMERIC MATERIALS

(71) Applicant: Commonwealth Scientific and Industrial Research Organisation, Acton (AU)

(72) Inventors: Florian Hans Maximilian Graichen, Richmond (AU); Benjamin Aldo Leita, Rowville (AU); Michael Shane O'Shea, Mulgrave (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/943,827

(22) Filed: Nov. 17, 2015

(65) Prior Publication Data

US 2016/0075716 A1 Mar. 17, 2016

Related U.S. Application Data

(63) Continuation of application No. 13/513,524, filed as application No. PCT/AU2010/001628 on Dec. 2, 2010, now Pat. No. 9,212,257.

(30) Foreign Application Priority Data

Dec. 4, 2009 (AU) ................................ 2009905928

(51) Int. Cl.
*C07D 493/08* (2006.01)
*C08G 63/672* (2006.01)
(Continued)

(52) U.S. Cl.
CPC ....... *C07D 493/08* (2013.01); *C08G 18/3212* (2013.01); *C08G 18/3218* (2013.01);
(Continued)

(58) Field of Classification Search
CPC .............. C07D 493/08; C08G 18/3212; C08G 18/3218; C08G 18/4213; C08G 18/73;
(Continued)

(56) References Cited

U.S. PATENT DOCUMENTS 9,212,257 B2 12/2015 Graichen et al.
2012/0238706 A1 9/2012 Graichen et al.

FOREIGN PATENT DOCUMENTS

WO WO 2009/039407 A1 3/2009
WO WO 2010/078328 A3 7/2010

OTHER PUBLICATIONS

Easton et al. Fabrication and Characteristics of Polymer Thin-films Derived from Cineole Using Radio Frequency Plasma Polymerisation. Polymer, (2009) 50, 3465-3469.
(Continued)

*Primary Examiner* — Ling Choi
*Assistant Examiner* — Gennadiy Mesh
(74) *Attorney, Agent, or Firm* — John P. White; Cooper & Dunham LLP

(57) ABSTRACT

Monomers having the structure and a polymer comprising as part of its polymer backbone a moiety of Formula (II):

Formula (II)

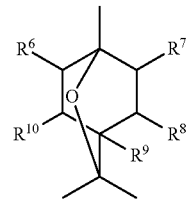

where one of $R^6$ to $R^{10}$ represents A-O— and one of $R^6$ to $R^{10}$ represents —O—B and the remainder of $R^6$ to $R^{10}$ represent H, where A and B represent the remainder of the polymer backbone and may be the same or different. The monomers are diol, dicarboxylic acid, epoxy, and succinate compounds containing a cineole structure wherein a compound for use in preparation of polymer, the compound selected from

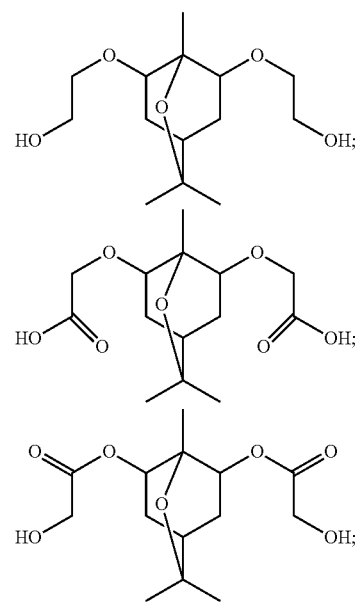

(Continued)

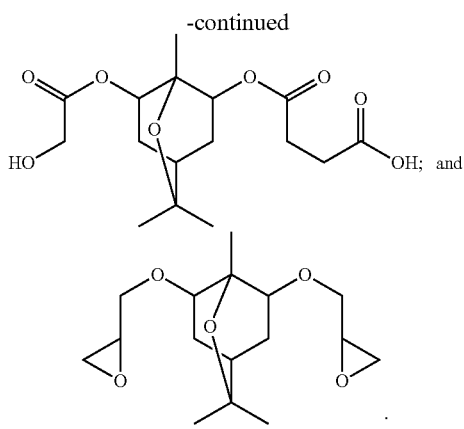

(51) Int. Cl.
    *C08G 69/26* (2006.01)
    *C08G 18/73* (2006.01)
    *C08G 18/76* (2006.01)
    *C08G 18/32* (2006.01)
    *C08G 18/42* (2006.01)

(52) U.S. Cl.
    CPC ......... *C08G 18/4213* (2013.01); *C08G 18/73* (2013.01); *C08G 18/7621* (2013.01); *C08G 18/7671* (2013.01); *C08G 63/672* (2013.01); *C08G 69/26* (2013.01)

(58) Field of Classification Search
    CPC ............ C08G 18/7621; C08G 18/7671; C08G 63/672; C08G 69/26
    See application file for complete search history.

(56) References Cited

OTHER PUBLICATIONS

Bozell et al. New Chemicals and Polymers from Renewable Resources. Fuel Chemistry Division Preprints, (2002) 47(1), 359-360.
Leita et al. Production of P-cymene and Hydrogen from a Biorenewable Feedstock-1, 8-cineole (eucalyptus oil). Green Chem., (2009) 12, 70-76.
International Search Report, mailed Jan. 21, 2011 in connection with PCT International Application No. PCT/AU2010/001628, filed Dec. 2, 2010.
Written Opinion of the International Searching Authority, mailed Jan. 21, 2011, in connection with PCT International Application No. PCT/AU2010/001628, filed Dec. 2, 2010.
International Preliminary Report on Patentability (Chapter I of the Patent Cooperation Treaty), including Written Opinion of the International Search Authority, issued Jun. 5, 2012 in connection with PCT International Application No. PCT/AU2010/001628, filed Dec. 2, 2010.

1 Claim, No Drawings

POLYMERIC MATERIALS

RELATED APPLICATIONS

This application is a continuation of U.S. Ser. No. 13/513,524, filed Jun. 1, 2012, which is a §371 national stage of PCT International Application No. PCT/AU2010/001628, filed Dec. 2, 2010, which claims the priority of Australian Provisional Application No. 2009905928, filed Dec. 4, 2009, the contents of each of which are hereby incorporated by reference in their entirety into this application.

FIELD OF THE INVENTION

The present invention relates to polymeric materials, and in particular to polymeric materials prepared using a cyclic compound derived from a renewable source.

BACKGROUND OF THE INVENTION

There is a continuing demand for new polymeric materials with new and useful properties. The majority of synthetic polymers are formed from the polymerisation of compounds derived from the petroleum industry. The volatile price of oil, combined with its non-renewable nature, has led to a considerable amount of research effort being directed towards discovering alternate sources of compounds for use in polymer synthesis. One such source that has received continuing interest is biologically derived material that can function as, or be converted into, industrially useful compounds for use in polymer synthesis. The renewable nature of many biologically derived materials makes them particularly attractive.

Unfortunately, however, many biologically derived materials do not possess properties that would otherwise make them suitable compounds for polymer synthesis. For example many biologically derived materials, such as unsaturated vegetable oils, typically do not possess useful functionality (such as amino, hydroxyl, carboxy groups and suitably reactive double bonds) that readily allow for polymerisation to take place. In the course of synthetically installing such useful functionality, through oxidation of one or more double bonds to form hydroxyl groups for example, the mechanical properties of the biologically derived materials are often adversely modified. On the other hand, some biologically derived materials may possess useful functionality for polymerisation but may not possess other structural features providing desirable properties for new and useful polymeric materials.

An opportunity therefore exists to provide polymers with new and useful properties which have been prepared using compounds derived from a renewable source.

SUMMARY OF THE INVENTION

It has now been found that a particular class of cyclic compound of Formula (I) can advantageously be used in the preparation of polymeric materials:

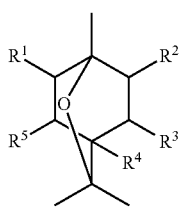

Formula (I)

where one of $R^1$ to $R^5$ represents X—O—, one of $R^1$ to $R^5$ represents —O—Y, and the remainder of $R^1$ to $R^5$ represent H, where X and Y may be the same or different and represent H or a group comprising reactive functionality. In some embodiments, X and Y may be independently selected from H and optionally substituted hydroxyalkyl, hydroxyalkyl carbonyl, aminoalkyl, aminoalkylcarbonyl, carboxyalkyl, carboxyalkylcarbonyl, epoxyalkyl and unsaturated variants thereof such as aminoalkylene. In one embodiment X and Y are each H.

Compounds of Formula (I) can advantageously be derived from a number of naturally occurring or semi-synthetic sources including α-pinene and sobrerol, which in turn may be sourced from a range of renewable plant sources such as pine, bay, tea tree, mugwort, sweet basil, wormwood, rosemary, sage and Eucalyptus.

In one aspect, the invention therefore provides a polymer comprising as part of its polymer backbone a moiety of Formula (II):

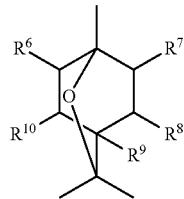

Formula (II)

where one of $R^6$ to $R^{10}$ represents A-O—, one of $R^6$ to $R^{10}$ represents —O—B, and the remainder of $R^6$ to $R^{10}$ represent H, where A and B represent the remainder of the polymer backbone and may be the same or different.

In a further aspect, the present invention provides a product (such as a sheet, fibre or film) comprising the polymer of the invention.

In another aspect, the present invention provides a polymer blend comprising the polymer of the invention and at least one other polymer. In some embodiments the polymer blend may be a physical blend. In some embodiments the polymer blend may be a melt mixed blend.

In yet a further aspect, the present invention provides for use of a compound of Formula (I) in the preparation or modification of polymer:

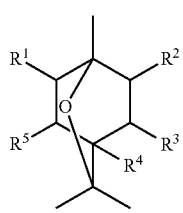

Formula (I)

where one of $R^1$ to $R^5$ represents X—O—, one of $R^1$ to $R^5$ represents —O—Y, and the remainder of $R^1$ to $R^5$ represent H, where X and Y may be the same or different and represent H or a group comprising functionality which is capable of reacting with one or more monomers and/or with one or more polymers.

By a compound of Formula (I) being used in the "preparation" of polymer is meant that the compound of Formula (I) reacts with one or more monomers to form polymer covalently incorporating the reacted residue of the compound of Formula (I).

By a compound of Formula (I) being used in the modification of polymer is meant that the compound of Formula (I) reacts with one or more polymers and becomes covalently coupled thereto.

By a compound of Formula (I) being "capable of reacting with one or more monomers or one or more polymers" is meant that the compound of Formula (I) and the one or more monomers and/or the one or more polymers will have compatible chemical functionality that can undergo reaction. For example, polymer may be prepared by functional groups of the compound of Formula (I) reacting with functional groups of one or more monomers (e.g. via a polymerisation reaction). As a further example, polymer may be modified by functional groups of the compound of Formula (I) reacting with functional groups of the one or more polymers that is to be modified. Such reactions may be promoted by any suitable means, for example by melt mixing the components or by combining the components in a suitable solvent.

In a further aspect, the invention provides a process for preparing polymer or modifying polymer, the process comprising reacting a compound of Formula (I):

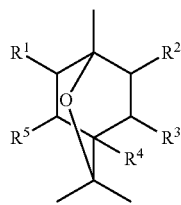

Formula (I)

with monomer and/or polymer, where one of $R^1$ to $R^5$ represents X—O— and one of $R^1$ to $R^5$ represents —O—Y and the remainder of $R^1$ to $R^5$ represent H, where X and Y may be the same or different and represent H or a group comprising functionality which is capable of reacting with the monomer and polymer.

By a compound of Formula (I) "reacting" with monomer and/or polymer is meant that the compound of Formula (I) reacts with and becomes covalently coupled to the monomer and/or polymer.

By a compound of Formula (I) being "capable of reacting with the monomer and polymer" is meant that the compound of Formula (I) and the monomer and the polymer will have compatible chemical functionality that can undergo reaction. In other words, each of the monomer and the polymer will have compatible chemical functionality that can undergo reaction with relevant functional groups of the compound of Formula (I). For example, polymer may be prepared by functional groups of the compound of Formula (I) reacting with functional groups of the monomer (e.g. via a polymerisation reaction). As a further example, polymer may be modified by functional groups of the compound of Formula (I) reacting with functional groups of the polymer that is to be modified. Such reactions may be promoted by any suitable means, for example by melt mixing the components or by combining the components in a suitable solvent.

In another aspect, the present invention provides for use of a polymer, which comprises as part of its polymer backbone a moiety of Formula (II), to modify one or more other polymers:

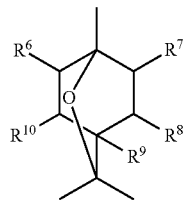

Formula (II)

where one of $R^6$ to $R^{10}$ represents A-O— and one of $R^6$ to $R^{10}$ represents —O—B and the remainder of $R^6$ to $R^{10}$ represent H, where A and B represent the remainder of the polymer backbone and may be the same or different.

For convenience, polymer which comprises as part of its polymer backbone a moiety of Formula (II) may herein be referred to as the "polymer of Formula (II)".

By a polymer of Formula (II) being used to modify one or more other polymers is meant that the physical and/or chemical properties of the one or more other polymers are altered by the polymer of Formula (II).

Modification of the one or more other polymers may be non-reactive or reactive in nature. For example, modification may be achieved by melt mixing or blending the one or more other polymers that is to be modified with the polymer of Formula (II). The resulting melt mixed polymer composition may be an intimate and integral blend of each polymer (i.e. non-reactive in nature), or it may comprise polymer that has formed as a result of a reaction between the polymers (i.e. reactive in nature). Where the modification is reactive in nature, the polymer of Formula (II) and the one or more other polymers will of course have compatible chemical functionality that can facilitate the reaction.

In a yet further aspect, the present invention provides a process for modifying polymer, the process comprising combining a polymer which comprises as part of its polymer backbone a moiety of Formula (II),

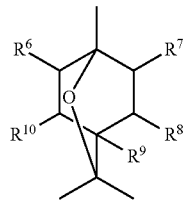

Formula (II)

with one or more other polymers, where one of $R^6$ to $R^{10}$ represents A-O— and one of $R^6$ to $R^{10}$ represents —O—B and the remainder of $R^6$ to $R^{10}$ represent H, where A and B represent the remainder of the polymer backbone and may be the same or different.

By "modifying polymer" in this aspect is meant that the physical and/or chemical properties of the one or more other polymers are altered upon combining it with the polymer of Formula (II).

By "combining" a polymer of Formula (II) with the one or more other polymers is meant that all polymers are combined such that the physical and/or chemical properties of the one or more other polymers to be modified are altered. Combining the polymers to achieve this will generally be performed in a liquid state, for example by melt mixing the polymers or by dissolving the polymers in a suitable solvent(s).

The act of combining the polymers may be reactive or non-reactive in nature as described herein in connection with the modifying polymer.

In a still further aspect, the present invention provides a process for producing polymer comprising as part of its polymer backbone a moiety of Formula (II):

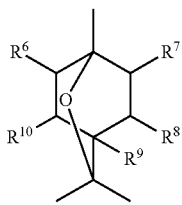

Formula (II)

where one of $R^6$ to $R^{10}$ represents A-O— and one of $R^6$ to $R^{10}$ represents —O—B and the remainder of $R^6$ to $R^{10}$ represent H, where A and B represent the remainder of the polymer backbone and may be the same or different, the process comprising polymerising one or more compounds of Formula (I) with monomer:

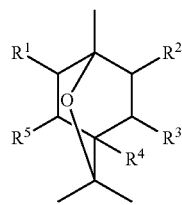

Formula (I)

where one of $R^1$ to $R^5$ represents X—O— and one of $R^1$ to $R^5$ represents —O—Y and the remainder of $R^1$ to $R^5$ represent H, where X and Y may be the same or different and represent H or a group comprising functionality which is capable of reacting with the monomer.

By the compound of Formula (I) having "a group comprising functionality which is capable of reacting with the monomer" is meant that the group will have compatible chemical functionality that can react with the monomer so as to form the polymer.

Accordingly, the expression "compatible chemical functionality" is intended to mean that the group and the monomer have functionality of a type that can react with each other so as to form the polymer.

The compounds of Formula (I) may react with themselves or other compounds of Formula (I) to form polymer. In other words, compounds of Formula (I) may polymerised in there own right, or with co-monomers not of Formula (I), to form polymer.

For avoidance of any doubt, the "moiety of Formula (II)" is intended to be a reference to:

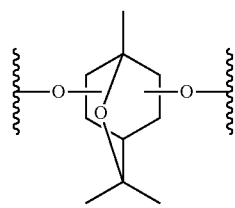

with A and B being presented in Formula (II) to (i) more clearly depict that the "moiety" forms part of the polymer backbone, and (ii) define the nature of the remainder of the polymer backbone. As mentioned, polymer which comprises as part of its polymer backbone a moiety of Formula (II) may for convenience herein be referred to as a "polymer of Formula (II)".

As used herein, the expression forming "part of the polymer backbone" means that the moiety of Formula (II) (i.e. excluding A and B) is part of the string of atoms that are each connected so as to form the polymer chain (i.e. including A and B) which may be linear or branched. In other words, the moiety of Formula (II) is not pendant from the polymer backbone. Despite the moiety of Formula (II) not being pendant from the polymer backbone, the polymers of the invention may still comprise a pendant group which is formed from the compound of Formula (I), so long as the polymer backbone comprises at least one moiety of Formula (II).

Examples of A and B are discussed in more detail below, but include polyurethane, polycarbonate and polyester polymer chains, polyether-polyurethane, polyester-amides, polyether-polyesters and polyether-amides.

Depending on the application, the polymer of the invention may have a single moiety of Formula (II), but more typically the polymer will comprise a plurality of moieties of Formula (II) (e.g. 10 or more, 25 or more, 50 or more, 100 or more). Typically each of the plurality of moieties of Formula (II) shall be located in the polymer backbone. In polymers comprising a plurality of moieties of Formula (II), each moiety of Formula (II) may be the same or different and each group represented by A and B may be the same or different.

For example, the moiety of Formula (II) may, in conjunction with a suitable comonomer, form a repeat unit of a polyester or polyurethane as illustrated below in general formula (IIa) and (IIb), respectively:

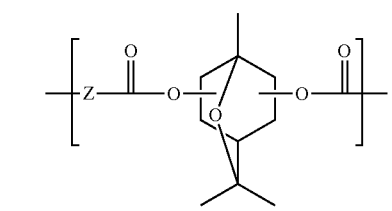

(IIa)

where Z is an alkyl, aryl or alkylaryl group wherein, for each repeat unit of the polyester, Z and the moiety of Formula (II) may each independently be the same or different;

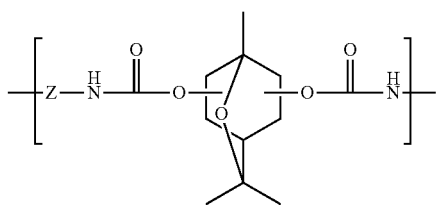

(IIb)

where Z is an alkyl, aryl or alkylaryl group wherein, for each repeat unit of the polyurethane, Z and the moiety of Formula (II) may each independently be the same or different.

Compounds of Formula (I) can be effectively and efficiently used to prepare new polymer materials. Compounds of Formula (I) can advantageously be prepared from a renewable source and polymer derived from them have been found to exhibit improved stiffness or rigidity relative to polymers prepared using conventional monomers, including diols such as ethylene glycol.

Further aspects of the invention are described in more detail below.

DETAILED DESCRIPTION OF THE INVENTION

A cyclic compound of Formula (I) may for convenience otherwise be referred to herein as cineole compound. More particularly, where X and Y are each H, the cineole compound may be referred to as cineole diol. The structure of cineole is shown below:

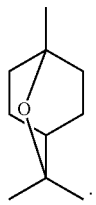

Cineole is a natural product that may be isolated from a number of natural renewable sources. For example, cineole makes up approximately 90% of Eucalyptus oil which is distilled primarily from the leaves of trees from the genus Eucalyptus.

It will be understood, however, that despite the structural similarity of compounds of Formula (I) to cineole it may be more facile to synthesise compounds of Formula (I) from compounds that have a greater degree of chemical functionality than cineole. Typically this chemical functionality will enable the introduction of the two exocyclic oxygen atoms that are present in compounds of Formula (I). By "exocyclic oxygen atoms" in compounds of Formula (I) is meant the oxygen atoms in "X—O—" and "—O—Y", to the exclusion of any oxygen atoms that may be present in X and/or Y. These exocyclic oxygen atoms are highlighted in the following structure, which is provided as an example of the compound of Formula (I):

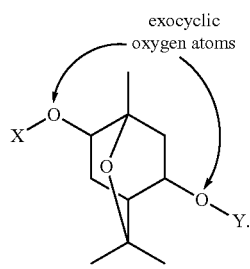

For example, compounds of Formula (I) may be derived from a number of sources including the following compounds:

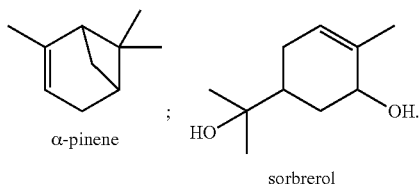

α-pinene ; sorbrerol

Each of α-pinene and sobrerol possess one or more functional groups, in particular a double bond, that may enable the introduction of the two exocyclic oxygen atoms which are present in compounds of Formula (I).

These compounds may be isolated from a number of natural sources including pine, bay, tea tree, mugwort, sweet basil, wormwood, rosemary, sage and Eucalyptus. Particularly good sources of the compounds are: α-pinene from pine oil, Eucalyptus oil and Kunzea oil; and sorbrerol from a number of natural sources and also semi-synthetically from the oxidation of a terpenoid starting material such as α-pinene. Each of these natural sources is believed to be renewable. In fact, many of these natural sources are harvested in significant commercial quantities.

Those skilled in the art will appreciate that compounds of Formula (I) and Formula (II) will exist in a number of isomeric forms (such as stereoisomers and structural isomers). In particular, the compounds of the invention (including monomers and polymers) may exist in one or more stereoisomeric forms (such as enantiomers, diastereomers) and the two exocyclic oxygen atoms may be located at any two of $R^1$ to $R^5$ (oxy structural isomers) producing substituents A-O— and —O—B at any two of $R^6$ to $R^{10}$ following polymerisation. The present invention includes within its scope all of these stereoisomeric forms and oxy structural isomers (and polymers derived therefrom) either isolated (in for example enantiomeric isolation) or in combination (including racemic mixtures and polymers derived from mixtures of oxy structural isomers). Although specific features of an isomer of Formula (II) are not particularly important to the working of the invention, it may be the case that certain compounds can be more readily prepared with a particular isomeric structure.

In some embodiments X and Y may be independently selected from H and optionally substituted hydroxyalkyl, hydroxyalkylcarbonyl, aminoalkyl, aminoalkylcarbonyl, carboxyalkyl, carboxyalkylcarbonyl, epoxyalkyl and unsaturated variants thereof such as aminoalkylene. In these cases each alkyl group, or unsaturated variant thereof, may comprise from 2 to 20, or from 2 to 10 carbon atoms.

In some embodiments, compounds of Formula (I) have a structure selected from the following:

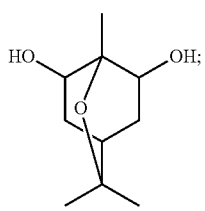

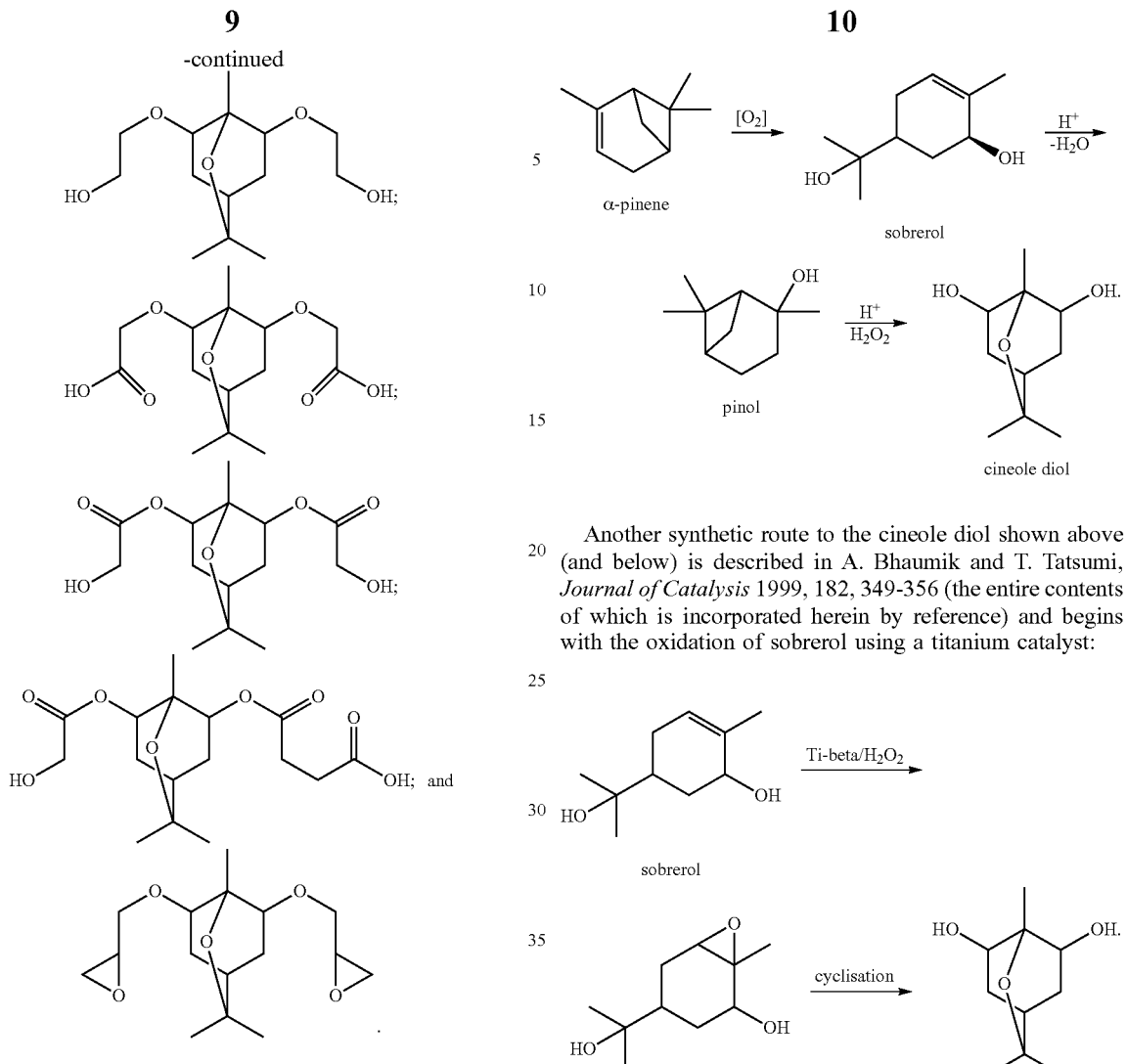

In one embodiment X and Y are each H and the compound of Formula (I) has the following general structure:

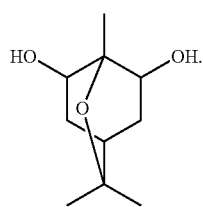

One particular compound of Formula (I) is known as epomediol or (6R,7S)-1,3,3-trimethyl-2-oxabicyclo[2.2.2]octane-6,7-diol.

Whilst the present invention envisages that compounds of Formula (I) may be derived by any suitable means, synthetic methodologies which may be used to prepare a specific cineole compound of Formula (I), where X and Y are each H, are outlined below by way of example only.

As described in L. A. Popova, V. I. Biba, V. M. Prishchepenko, S. V. Shavyrin and N. G. Kozlov., translated from *Zhurnal Obshch Khimii* 1991, 62(7), 1639-1645 (the entire contents of which is incorporated herein by reference) the cineole diol shown below is derived from α-pinene (via sobrerol):

Another synthetic route to the cineole diol shown above (and below) is described in A. Bhaumik and T. Tatsumi, *Journal of Catalysis* 1999, 182, 349-356 (the entire contents of which is incorporated herein by reference) and begins with the oxidation of sobrerol using a titanium catalyst:

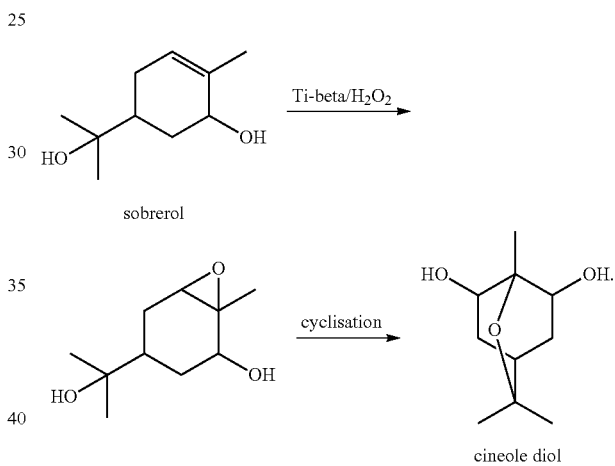

The two groups X—O— and —O—Y provide functionality to covalently couple the cyclic moiety of compounds of Formula (I) into the polymer backbone. For example, where X and Y are each H the cineole compound is provided with two reactive hydroxyl groups which are available for reaction with a monomer or polymer having compatible chemical functionality.

In some embodiments, it may be desirable to adjust the reactivity of the X and/or Y groups for a given polymerisation. For example, it will be appreciated that when X and Y are H, the resultant secondary alcohol groups are quite close to the cyclic moiety which may reduce the reactivity of the alcohol groups due to steric hindrance. Where X and Y are each hydroxyalkyl groups (such as hydroxyethyl groups) the compound of Formula (I) is similarly provided with two reactive hydroxyl groups which, in this case, are primary alcohol groups and are linked to the cyclic moiety of Formula (I) through alkyl groups and the exocyclic oxygen atoms of Formula (I). In that case the primary alcohol groups will generally be more reactive toward polymerisation than the secondary alcohol groups.

In another example, where X and Y are each carboxyalkylcarbonyl groups the compound of Formula (I) is provided with two reactive carboxylic acid groups which are linked to the cyclic moiety of Formula (I) through alkyl groups and ester groups which comprise the exocyclic oxygen atoms of Formula (I). It will be understood that a carboxylic acid group is typically electrophilic in reactivity whereas a hydroxyl group is typically nucleophilic in reactivity, and accordingly the X and Y groups may be chosen to provide the compound of Formula (I) with the desired reactivity.

Combinations of reactive functional groups, such as where X is a hydroxyalkyl group and Y is a carboxyalkylcarbonyl group are also envisaged. In each case, the reactive functionality is capable of reacting with a monomer having compatible chemical functionality.

In one embodiment, Formula (I) is represented by the compound:

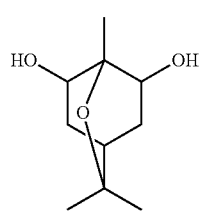

and this compound is polymerised with a monomer having compatible chemical functionality (e.g. a diacid) to form a polymer comprising as part of its polymer backbone a moiety:

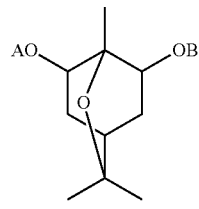

where A and B represent the remainder of the polymer backbone and may be the same or different.

In another embodiment Formula (I) is represented by the compound:

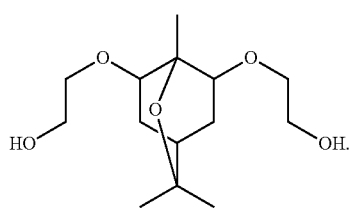

In that case, each of X and Y represent hydroxyethyl groups. Those skilled in the art will appreciate that the hydroxyethyl groups may be further derivatised such that one or both of the hydroxyl groups are converted into, for example, acid, amine or cyano groups. For example, the hydroxyethyl derivative may be synthesised as shown below from cineole diol, and may be further oxidised to form a di-carboxylic acid compound:

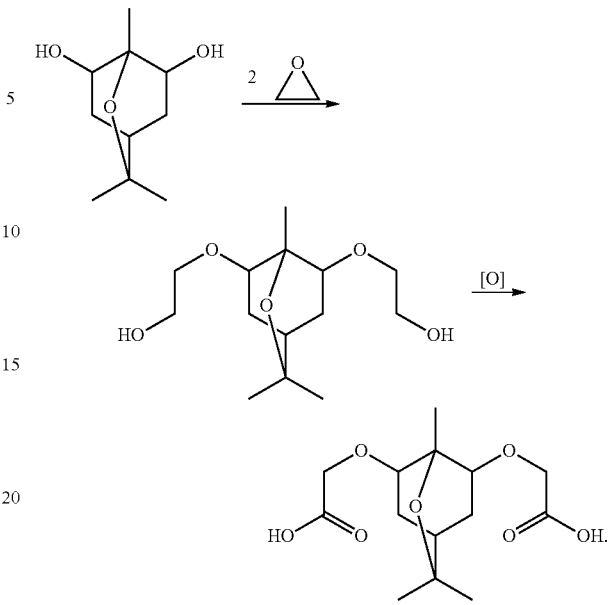

In a further embodiment, Formula (I) is represented by the compound:

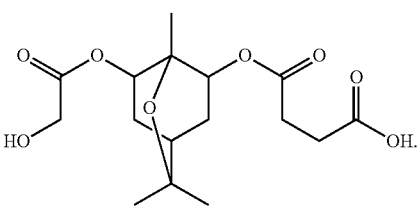

In that case, X represents hydroxymethylcarbonyl and Y represents carboxyethylcarbonyl. It will be appreciated that this compound may be synthesised as shown below from cineole diol:

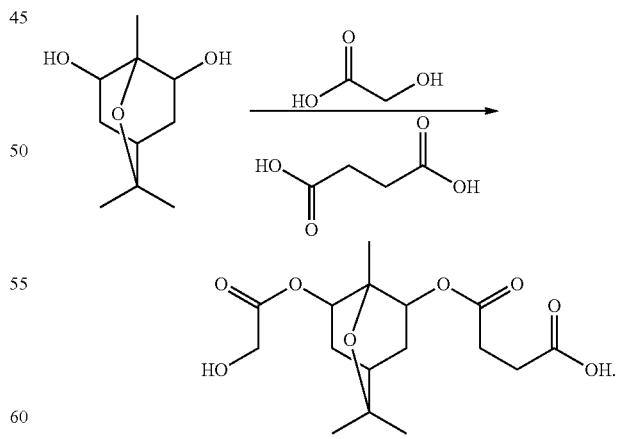

This acid-alcohol compound may self polymerise or be polymerised with a co-monomer comprising compatible chemical functionality (e.g. an acid-alcohol) to form a polymer comprising as part of its polymer backbone a moiety:

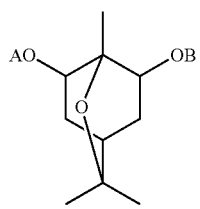

where A and B represent the remainder of the polymer backbone and may be the same or different.

In some embodiments, it will be appreciated that a homopolymer may be formed. In that respect, where the substituent X—O— of Formula (I) is capable of reacting with the substituent —O—Y of Formula (I) a homopolymer may be formed. In the acid-alcohol example directly above X—O— is capable of reacting with —O—Y to form a ester linkage. Accordingly the monomer may be self polymerised to form a homopolymer that will be a polyester in this instance.

The expression "compatible chemical functionality" used herein therefore refers to chemical functionality of, for example a monomer or a polymer, that is capable of undergoing reaction (such as polymerisation, chain coupling etc) with reactive functionality of X—O— and/or —O—Y in a compound of Formula (I). The reactive functionality in the X—O— and/or —O—Y groups of compounds of Formula (I) may react with a variety of functional groups. For example, where X and Y are both H, or X—O— and —O—Y comprise hydroxy groups, the hydroxy groups may react with such functional groups as: isocyanate functionality to form carbamate or urethane linkages; carboxylic acid functionality to produce ester linkages; carboxylic acid halide functionality to produce ester linkages; ester functionality to produce new ester linkages; anhydride functionality to produce ester linkages; epoxide functionality to produce ether linkages; alkyl halide functionality to produce ether linkages; as well as other carboxylic acid derivatives (including carbon dioxide and phosgene) to produce carbonate linkages. Accordingly, the expression "compatible chemical functionality" includes functionality or groups such as isocyanate, carboxylic acid, carboxylic acid derivatives such as carboxylic acid halide, ester, anhydride and other carboxylic acid derivative groups.

In other embodiments, the X—O— and/or —O—Y groups may comprise carboxylic acid functionality, which is capable of undergoing reaction with "compatible chemical functionality" such as amines, alcohols and acid halides. Likewise the X—O— and/or —O—Y groups may comprise epoxide functionality, which is capable of undergoing reaction with "compatible chemical functionality" such as amines, alcohols and thiols.

Accordingly, the expression "monomer having compatible chemical functionality" or similar expressions such as "monomer which has compatible chemical functionality" used herein includes monomer comprising one or more chemical functional groups such as isocyanate, carboxylic acid, carboxylic acid derivatives (including carboxylic acid halide, ester, anhydride groups), amine, alcohol, thiol and combinations thereof selected as appropriate depending on the nature of the X and/or Y groups in Formula (I). Examples of such monomers are polyisocyanates, poly(acid halides), polyacids, carbon dioxide, phosgene (or triphosgene), polyols, polyamines and polythiols. In each of these cases the prefix "poly" is used to indicate the presence of 2 or more (for example in the case of a polyisocyanate, 2 or more isocyanate groups) reactive functional groups. Typically the monomers will comprise 2 reactive functional groups, such as a diisocyanate, diacid halide or a diacid. Co-monomers that react with compounds of Formula (I) to form polymer may also be of Formula (I).

In some embodiments the or each "monomer" which is used to react with a compound of Formula (I) in the polymerisation reaction to form the polymer may contain at least one group of compatible chemical functionality (as defined herein) in addition to at least one group which is not, of itself, compatible for undergoing reaction with the compound of Formula (I). Examples of such monomers are hydroxy-acids, amino acids and thio acids. In the case of a hydroxy-acid, the carboxylic acid is capable of reacting with a hydroxy group of compounds of Formula (I) (such as when X and/or Y are H) to produce a hydroxy-terminated compound. Likewise in the case of an amino acid, the carboxylic acid is capable of reacting with a hydroxy group of compounds of Formula (I) (such as when X and/or Y are H) to produce an amino-hydroxy-terminated compound. Likewise in the case of a thio acid, the carboxylic acid is capable of reacting with a hydroxy group of compounds of Formula (I) (such as when X and/or Y are H) to produce a thio-hydroxy-terminated compound. These hydroxy/amino/thio terminated compounds may subsequently undergo reaction with another monomer bearing a carboxylic acid, isocyanate group, etc. so that the polymer backbone may comprise one or more ester, amide, thioester, urea, urethane and/or thiocarbamate functional groups. Other monomers may be used which contain functionality which undergoes ring opening to produce a functional group which is not, of itself, compatible for undergoing reaction with compounds of Formula (I). Examples of such monomers are lactones, lactams, cyclic carbonates and cyclic ethers such as epoxides. For example, where X is H, the hydroxyl group may react with a lactone compound such as y-butyrolactone to produce a hydroxyl-terminated compound.

The "remainder" of the polymer backbone, which is represented by A and B, may be any type of polymer, examples of which are: polyurethanes; polyesters (e.g. PET (polyethylene terephthalate), PLGA (poly(lactic-co-glycolic acid)), PLA (polylactic acid), PGA (polyglycolic acid), PHB (polyhydroxybutyrate), PCL (polycaprolactone); and copolymers thereof); polyamides; polycarbonates; polyimides; polyethers; polyepoxys; polyacrylates; polysiloxanes; polyvinyls (e.g. polyvinylalcohol, polyvinylacetate) and combinations thereof. In some embodiments, A and B are each selected from: polyurethanes; polyesters; polyethers; polycarbonates; and combinations thereof. In one embodiment A and/or B represent a polyurethane or polyester. In all cases, A and/or B may comprise a polymerised residue of one or more compounds of Formula (I). For example, A and/or B may be a poly(ethylene-co-cineole diol) terephthalate.

Polymer comprising a moiety of Formula (II) may be linear or branched. Polymer comprising a moiety of Formula (II) may be a crosslinked polymer. Crosslinked polymer may be formed, for example, by the introduction of unsaturation into the polymer backbone or pendant from the polymer backbone, from the use of maleic anhydride or vinyl ester, followed by free radical crosslinking Those skilled in the art will appreciate that this form of crosslinking generally requires the use of a free radical initiating source. Crosslinked polymer may also be formed by the introduction of pendant epoxy groups which may be crosslinked using a polyamine.

In some embodiments, the polymer formed may be a linear polyurethane. A linear polyurethane may be synthesised using equal molar amounts of a diol component and a diisocyanate component. In one embodiment of the invention the diol component consists 100% of the cyclic compound of Formula (I) bearing two hydroxyl groups, such as when X and Y are both H. In this instance, polymerisation of the cyclic compound of Formula (I) with a diisocyanate produces a polyurethane comprising 50 mol % cyclic compound residue and 50 mol % diisocyanate residue. In a further embodiment, the diol component may comprise a plurality of diol compounds where each compound may comprise from 1 to 99 mol % of the diol component. In such an embodiment it will be understood that the combined total of the diol compounds will add to 100 mol %. For example the diol component may comprise 50 mol % of a cyclic compound of Formula (I) bearing two hydroxyl groups and 50 mol % of another diol (e.g. ethylene glycol). Likewise, the diisocyanate component may consist of a single compound or may comprise two or more diisocyanate compounds where each compound may range from 1 to 99 mol % of the diisocyanate component. Similarly, it will be understood that in such an embodiment the combined total of the diisocyanate compounds will add to 100 mol %.

In some embodiments the polymer formed is a linear polyester. A linear polyester may be synthesised from equal molar amounts of a diol component and a diacid component (or diester or diacid halide as appropriate). In some embodiments the diol component consists 100% of the cyclic compound of Formula (I) bearing two hydroxyl groups, such as when X and Y are both H. In this instance, polymerisation of the cyclic compound of Formula (I) with a diester produces a polyester comprising 50 mol % cyclic diol residue and 50 mol % diacid residue. In other embodiments the diol component may consist of a plurality of diol compounds where each compound may comprise from 1 to 99 mol % of the diol component. In these embodiments it will be understood that the combined total of each of the plurality of diol compounds is 100 mol % of the diol component. For example the diol component may consist 50 mol % of a cyclic compound of Formula (I) bearing two hydroxyl groups and 50 mol % of another diol. Likewise, the diacid component may consist of a single compound or may consist of one or more diacid compounds where each compound may range from 1 to 99 mol % of the diacid component. In these embodiments it will be understood that the combined total of each of the plurality of diacid compounds is 100 mol % of the diacid component.

Examples of polyisocyanates that may be used to prepare polymers of the invention include aliphatic, aromatic and cycloaliphatic polyisocyanates and combinations thereof. Specific polyisocyanates include, but are not limited to, diisocyanates such as m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,3-cyclohexane diisocyanate, 1,4-cyclohexane diisocyanate, hexahydro-toluene diisocyanate and its isomers, isophorone diisocyanate, dicyclo-hexyl-methane diisocyanates, 1,5-napthylene diisocyanate, 4,4'-diphenylmethane diisocyanate, 2,4' diphenylmethane diisocyanate, 4,4'-biphenylene diisocyanate, 3,3'-dimethoxy-4,4'-biphenylene diisocyanate, and 3,3'-dimethyl-diphenylpropane-4,4'-diisocyanate; triisocyanates such as 2,4,6-toluene triisocyanate; polyisocyanates such as 4,4'-dimethyl-diphenylmethane-2,2',5,5'-tetraisocyanate, polymethylene polyphenyl-polyisocyanates and alkyl esters of lysine diisocyanate (for example ethyl ester of lysine diisocyanate—ELDI); and combinations thereof.

Examples of polyacids that may be used to prepare polymers of the invention include aliphatic, aromatic and cycloaliphatic polyacids and combinations thereof. Specific polyacids include, but are not limited to the following, oxalic acid, fumaric acid, maleic acid, succinic acid, glutaric acid, adipic acid, pimelic acid, suberic acid, azelaic acid, sebacic acid, phthalic acid, dodecanediacid, isophthalic acid, terephthalic acid, dodecylsuccinic acid, napthalene-2,6-dicarboxylic acid, naphthalene-2,7-dicarboxylic acid, cyclohexane dicarboxylic acid, fumaric acid, itaconic acid, malonic acid, mesaconic acid. Esters, carboxylic acid halides and anhydrides of the above diacids are also suitable in the process of the invention.

Examples of polyols that may be used in combination with the cineole compounds of Formula (I) (in those instances where they bear two hydroxyl groups) to prepare polymers of the invention include aliphatic glycols such as: ethylene glycol, propylene glycol, butane-1,4-diol; glycol ethers such as diethylene glycol, dipropylene glycol and the like; and higher functionality polyols materials such as glycerol, sorbitol, pentaerythritol; and polyester polyols such as polycaprloactone diols. Also suitable are dihydroxy compounds such as bisphenol-A and hydrogenated bisphenol-A. Generally, the polyol will have from 2 to 20 or 2 to 10 carbon atoms and 2 to 4 hydroxy groups.

Where a polyfunctional compound having more than two reactive functional groups (e.g. triol, tetraol, triacid, tetraacid, triisocyanate, tetraisocyanate, etc) is used in accordance with the invention, those skilled in the art will appreciate that the molar fractions required for each monomer in a given reaction will need to be adjusted accordingly. Such higher polyfunctional compounds (i.e. >2 functional groups) will also typically introduce a branch point within the resulting polymer backbone.

As foreshadowed above, polymerisation of cyclic compounds of Formula (I), which bear two hydroxyl groups, with a polyisocyanate or polyacid (or derivatives thereof such as an ester or acid halide) may also take place in the presence of one or more other types of other polyols. Certain polyols can be referred to in the art as chain extenders.

Examples of polyols known in the art as chain extending polyols include α,ω-alkanediols such as ethylene glycol, 1,3-propanediol and 1,6-hexanediol.

Techniques, equipment and reagents well known in the art can advantageously be used to prepare or modify polymers in accordance with the invention. The polymerisation/modification may be carried out in a range of different equipment including batch kettles, static mixers, injection moulders or extruders.

In some embodiments, it may be advantageous to heat the reagents prior to or during the reaction process to improve their solubility or to enhance their reactivity. A catalyst, such as a polycondensation catalyst, well known to those skilled in the art may be included in the reaction mixture to increase the rate of polymerisation. Typical condensation catalysts include Lewis acids such as antimony trioxide, titanium oxide and dibutyl tindilaurate.

The polymerisation may also be conducted in solvent to help increase the rate of polymerisation. The solvent will generally be selected to have only minimal solubility with any condensate (such as water or low molecular weight alcohol) which may be formed in the case of polyester formation. For example the reaction may be carried out in toluene and a toluene/condensate mixture distilled off continuously and the condensate allowed to separate in a Dean—Stark trap.

In some embodiments, polyurethanes may be prepared batch wise by mixing all components together and waiting until an exotherm occurs followed by casting the mixture into a container. The mixture can be subsequently heated to drive the reaction. When adopting this approach, the components to be mixed may first be made up into two parts before mixing: Part-1 may include a cyclic compound of Formula (I) bearing two hydroxyl groups and optionally one or more of a polyol, a chain extender, blowing agent (e.g. water), catalyst, and surfactants etc. Part-2 will generally comprise the polyisocyanate. Part-1 or Part-2 may also contain other additives such as fillers, pigments etc.

The polyurethanes may also be prepared as a prepolymer that is subsequently reacted with a chain extender. For example, through suitable adjustment of molar ratios, an isocyanate terminated pre-polymer may be prepared by mixing Parts-1 and -2 mentioned above. The isocyanate terminated polymer may then be reacted with a chain extender/branching molecule such as a short chain diol (e.g. 1,4-butanediol) or a higher polyol (such as a triol). Alternatively, through suitable adjustment of molar ratios, the prepolymer may be produced such that it is hydroxy terminated. This hydroxy terminated prepolymer may then be reacted with a polyisocyanate to produce the desired polyurethane.

Where polyesters are prepared using a carboxylic acid halide monomer, those skilled in the art will appreciate that the reaction is driven, at least in part, by the formation and removal of HX (where X is a halide). For example, if a diacid chloride comonomer is reacted with a compound of Formula (I) bearing two hydroxyl groups, HCl will be liberated from the reaction. Such a reaction may be carried out in solution at an elevated temperature to drive the reaction. It is also possible to add an appropriate base to form a salt with the liberated acid halide. For example an excess of triethylamine may be included in a reaction mixture containing a 1:1 molar ratio of a di-acid chloride co-monomer and a compound of Formula (I) bearing two hydroxyl groups. The reaction will afford the desired polymer and a triethylamine hydrochloride salt. Despite the fact that the reaction of an alcohol and an acid halide does not liberate a condensate such as water or alcohol, the formation of the ester product may nonetheless be regarded as a condensation reaction to the extent that a condensate is typically formed in the prior conversion of a carboxylic acid into the acid halide.

In a similar way to the expressions "monomer having compatible chemical functionality" and variants thereof such as "monomer which has compatible chemical functionality" are defined herein, the expressions "polymer having compatible chemical functionality" and variants thereof such as "polymer which has compatible chemical functionality" used herein refer to polymers having a functionality that can react with reactive functionality in a compound of Formula (I) or a polymer of Formula (II).

Examples of polymers that may be modified with a compound of Formula (I) or a polymer of Formula (II) in accordance with the invention include polyesters, polyurethanes and polycarbonates.

In that respect, the groups X—O— and/or —O—Y in cineole compounds of Formula (I) may be used to promote reaction with compatible chemical functionality present in one or more polymers. In particular, the cineole compounds may advantageously be used to modify the molecular structure and hence properties of preformed polymers.

The invention provides polymer blends comprising the polymer of the invention and at least one other polymer. Standard blending techniques may be used including melt mixing, such as extrusion. The polymer blend may also be a physical blend (i.e. non-melt mixed).

A compound of Formula (I) is used to react with and covalently couple to the polymer to be modified.

The polymer of Formula (II) may modify one or more other polymers by reaction or by simply being melt blended therewith.

Where a compound of Formula (I) or a polymer of Formula (II) reacts with and modifies the molecular structure of the one or more other polymers, a residue of the compound or a portion of the polymer of Formula (II) typically forms part of the modified polymer's backbone. For example, where the X—O— and —O—Y groups in the cineole compounds comprise hydroxyl groups the cineole compounds may react with, and become incorporated in, a polyester through alcoholysis. Such reactions may be promoted using reactive extrusion techniques known in the art. In that case, the cineole compounds may be melt mixed with a polyester to promote insertion of the diol within the backbone of the polyester. Other functionality within the X—O— and/or —O—Y groups may additionally or alternatively enable the insertion of the cineole compound of Formula (I) into the backbone of the one or more polymers.

Where the cineole compound of Formula (I) is used to modify a preformed polymer, the modification process can be carried out using equipment and techniques known by those skilled in the art. For example, the cineole compound may be melt mixed with one or more polymers using continuous extrusion equipment such as twin screw extruders, single screw extruders, other multiple screw extruders and Farell mixers. Semi-continuous or batch processing equipment may also be used to achieve melt mixing. Examples of such equipment include injection moulders, Banbury mixers and batch mixers. Static melt mixing equipment may also be used.

Reaction of the cineole compound of Formula (I) with a polymer, such as a polyester, may result in a reduction in the polymer's molecular weight. If desired, the molecular weight of the polymer can be subsequently increased using techniques known in the art. For example, where the polymer that is reacted with the cineole compound is a polyester, and the cineole compound bears two hydroxyl groups, the resulting reaction mixture may be subjected to a solid state polymerisation process.

Chain coupling agents may also be introduced in the reaction to offset any reduction in molecular weight. Such agents include polyfunctional acid anhydrides, epoxy compounds, oxazoline derivatives, oxazolinone derivatives, lactams, isocyanates, lactones and related species. In some embodiments, the compound of Formula (I) may itself comprise such functionality in the X—O— and —O—Y groups.

Examples of coupling agents also include one or more of the following:

Polyepoxides such as bis(3,4-epoxycyclohexylmethyl) adipate; N,N-diglycidyl benzamide (and related diepoxies); N,N-diglycidyl aniline and derivatives; N,N-diglycidylhydantoin, uracil, barbituric acid or isocyanuric acid derivatives; N,N-diglycidyl diimides; N,N-diglycidyl imidazolones; epoxy novolaks; phenyl glycidyl ether; diethyleneglycol diglycidyl ether; Epikote 815 (diglycidyl ether of bisphenol A-epichlorohydrin oligomer).

Polyoxazolines/Polyoxazolones such as 2,2-bis(-oxazoline); 1,3-phenylene bis(2-oxazoline-2), 1,2-bis(2-oxazolinyl-2)ethane; 2-phenyl-1,3-oxazoline; 2,2'-bis(5,6-dihydro-4H-1,3-oxazoline); N,N'-hexamethylenebis (carbamoyl-2- oxazoline; bis[5(4H)-oxazolone]; bis(4H-3,1benzoxazin-4-one); 2,2'-bis(H-3,1-benzozin-4-one).

Polyfunctional acid anhydrides such as pyromellitic dianhydride, benzophenonetetracarboxylic acid dianhydride, cyclopentanetetracarboxylic dianhydride, diphenyl sulphone tetracarboxylic dianhydride, 5-(2,5-dioxotetrahydro-3-furanyl)-3-methyl-3-cyclohexene-1,2-dicarboxylic dianhydride, bis(3,4-dicarboxyphenyl)ether dianhydride, bis(3,4-dicarboxyphenyl)thioether dianhydride, bisphenol-A bisether dianhydride, 2,2-bis(3,4-dicarboxyphenyl) hexafluoropropane dianhydride, 2,3,6,7-naphthalenetetracarboxylic acid dianhydride, bis(3,4-dicarboxyphenyl)sulphone dianhydride, 1,2,5,6-naphthalenetetracarboxylic acid dianhydride, 2,2',3,3'-biphenyltetracarboxylic acid, hydroquinone bisether dianhydride, 3,4,9,10-perylene tetracarboxylic acid dianhydride, 1,2,3,4-cyclobutanetetracarboxylic acid dianhydride, 3,4-dicarboxy-1,2,3,4-tetrahydrolnaphthalene-succinic acid dianhydride, bicyclo(2,2)oct-7-ene-2,3,5,6-tetracarboxylic acid dianhydride, tetrahydrofuran-2,3,4,5-tetracarboxylic acid dianhydride, 2,2-bis(3,4dicarboxyphenyl)propane dianhydride, 3,3',4,4'-biphenyltetracarboxylic acid dianhydride, 4,4'-oxydiphthalic dianhydride (ODPA), and ethylenediamine tetraacetic acid dianhydride (EDTAh). It is also possible to use acid anhydride containing polymers or copolymers as the acid anhydride component.

Preferred polyfunctional acid anhydrides include pyromellitic dianhydride, 1,2,3,4-cyclopentanetetracarboxylic acid dianhydride, 1,2,3,4-cyclobutanetetracarboxylic acid dianhydride and tetrahydrofuran-2,3,4,5-tetracarboxylic acid dianhydride. Most preferably the polyfunctional acid anhydride is pyromellitic dianhydride.

Polyacyllactams such as N,N'-terephthaloylbis(caprolactarn) and N,N'-terephthaloylbis(laurolactam).

The polymer of Formula (II) may be used to modify the molecular structure and hence properties of preformed polymers. For example, melt mixing a polymer of Formula (II) in the form of a polyester with a another polyester will generally lead to the incorporation of the cyclic moiety of Formula (II) into the preformed polyester. Such insertion may also result in a loss in molecular weight of the other polyester which may be offset as herein described.

In some embodiments, it may be desirable to promote a degree of control over the way in which the cyclic moiety of the polymer of Formula (II) is incorporated into the one or more other polymers, particularly with respect to the block character of the polymer of Formula (II) comprising the moiety or moieties to be incorporated. In these embodiments, it may be possible to retain any block character using a polymer of Formula (II) that can resist fragmentation under the conditions employed. For example, the polymer of Formula (II) may be a polyester having ester groups in the polymer backbone that are sterically hindered and resistant to transesterification.

Compounds of Formula (I) can provide polymers of the invention with one or more advantageous properties. Without wishing to be limited by theory it is believed that the bicyclic structure of the compound of Formula (I) provides the polymers with advantageous mechanical properties, such as stiffness or rigidity. It is also believed that these advantageous properties are enhanced when the molar fraction of the moiety of Formula (II) in the polymer backbone is increased.

The polymers of the invention may be formed into a range of products. Examples of such products are sheets, fibres and films which may be formed through injection moulding, extrusion moulding, rotation moulding, foam moulding, calendar moulding, blow moulding, thermoforming, compaction and melt spinning, for example.

This polymer of the invention may be blended with one or more additives typically suited to polymer production. Examples of such additives include extenders, UV stabilizers, antioxidants, lubricants, flow modifiers, pigments, dyes, colourants, fillers, plasticizers, optical brighteners, fire retardants, impact modifiers, reinforcing agents (such as glass fibres, kaolin, mica), anti-static agents, and blowing agents.

In this specification "optionally substituted" is taken to mean that a group may or may not be substituted or fused (so as to form a condensed polycyclic group) with one, two, three or more of organic and inorganic groups (i.e. the optional substituent) including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloarylalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloaryloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylacyl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups.

In some embodiments, it may be desirable that a group is optionally substituted with a polymer chain. An example of such a polymer chain includes a polyester, polyurethane, or copolymers thereof.

Preferred optional substituents include alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. $C_{1-6}$ alkoxy such as methoxy, ethoxy, propoxy, butoxy, cyclopropoxy, cyclobutoxy), halo, trifluoromethyl, trich1oromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$alkyl, cyano, nitro OC(O)$C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro OC(O)$C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. NHC(O)$CH_3$), phenylamino (wherein phenyl itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$ alkyl, and amino), nitro, formyl, -C(O)-alkyl (e.g. $C_{1-6}$ alkyl, such as acetyl), O—C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$alkyl, and amino), replacement of $CH_2$ with C=O, $CO_2H$, $CO_2$alkyl (e.g. $C_{1-6}$ alkyl such as methyl ester, ethyl ester, propyl ester, butyl ester), $CO_2$phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O)$C_{1-6}$ alkyl, and amino), CONHalkyl (e.g. $C_{1-6}$ alkyl such as methyl ester, ethyl ester, propyl ester, butyl amide) CONHdialkyl (e.g. $C_{1-6}$ alkyl) aminoalkyl (e.g., FIN $C_{1-6}$ alkyl-, $C_{1-6}$alkylHN—$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkyl$O_2CC_{1-6}$ alkyl-), aminoalkyl (e.g., $H_2N(O)CC_{1-6}$ alkyl-, H($C_{1-6}$ alkyl)N(O)C$C_{1-6}$ alkyl-), formylalkyl (e.g., OHC$C_{1-6}$alkyl-), acylalkyl (e.g., $C_{1-6}$ alkyl(O)C$C_{1-6}$ alkyl-), nitroalkyl (e.g., $O_2NC_{1-6}$ alkyl-), sulfoxidealkyl (e.g., $R^3$(O)S$C_{1-6}$ alkyl, such as $C_{1-6}$ alkyl(O)S$C_{1-6}$ alkyl-), sulfonylalkyl (e.g., $R^3$(O)$_2$S$C_{1-6}$ alkyl-such as $C_{1-6}$ alkyl(O)$_2$S$C_{1-6}$ alkyl-), sulfonamidoalkyl (e.g., 2HRN(O)S$C_{1-6}$ alkyl, H($C_{1-6}$ alkyl)N(O)S$C_{1-6}$ alkyl-).

As used herein, the term "alkyl", used either alone or in compound words denotes straight chain, branched or cyclic alkyl, for example $C_{1-40}$ alkyl, or $C_{1-20}$ or $C_{1-10}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl, tridecyl, tetradecyl, pentadecyl, hexadecyl, heptadecyl, octadecyl, nonoadecyl, eicosyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. Where an alkyl group is referred to generally as "propyl", butyl" etc, it will be understood that this can refer to any of straight, branched and cyclic isomers where appropriate. An alkyl group may be optionally substituted by one or more optional substituents as herein defined.

As used herein, term "alkenyl" denotes groups formed from straight chain, branched or cyclic hydrocarbon residues containing at least one carbon to carbon double bond including ethylenically mono-, di- or polyunsaturated alkyl or cycloalkyl groups as previously defined, for example $C_{2-40}$ alkenyl, or $C_{2-20}$ or $C_{2-10}$. Thus, alkenyl is intended to include propenyl, butylenyl, pentenyl, hexaenyl, heptaenyl, octaenyl, nonaenyl, decenyl, undecenyl, dodecenyl, tridecenyl, tetradecenyl, pentadecenyl, hexadecenyl, heptadecenyl, octadecenyl, nondecenyl, eicosenyl hydrocarbon groups with one or more carbon to carbon double bonds. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethylenically mono-, di- or polyunsaturated alkyl or cycloalkyl groups as previously defined, for example, $C_{2-40}$ alkenyl, or $C_{2-20}$ or $C_{2-10}$. Thus, alkynyl is intended to include propynyl, butylynyl, pentynyl, hexaynyl, heptaynyl, octaynyl, nonaynyl, decynyl, undecynyl, dodecynyl, tridecynyl, tetradecynyl, pentadecynyl, hexadecynyl, heptadecynyl, octadecynyl, nondecynyl, eicosynyl hydrocarbon groups with one or more carbon to carbon triple bonds. Examples of alkynyl include ethynyl, 1-propynyl, 2-propynyl, and butynyl isomers, and pentynyl isomers. An alkynyl group may be optionally substituted by one or more optional substituents as herein defined.

An alkenyl group may comprise a carbon to carbon triple bond and an alkynyl group may comprise a carbon to carbon double bond (i.e. so called ene-yne or yne-ene groups).

As used herein, the term "aryl" (or "carboaryl") denotes any of single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may be optionally substituted by one or more optional substituents as herein defined.

As used herein, the terms "alkylene", "alkenylene", and "arylene" are intended to denote the divalent forms of "alkyl", "alkenyl", and "aryl", respectively, as herein defined.

The term "halogen" ("halo") denotes fluorine, chlorine, bromine or iodine (fluoro, chloro, bromo or iodo). Preferred halogens are chlorine, bromine or iodine.

The term "carbocyclyl" includes any of non-aromatic monocyclic, polycyclic, fused or conjugated hydrocarbon residues, preferably $C_{3-20}$ (e.g. $C_{3-10}$ or $C_{3-8}$). The rings may be saturated, e.g. cycloalkyl, or may possess one or more double bonds (cycloalkenyl) and/or one or more triple bonds (cycloalkynyl). Particularly preferred carbocyclyl moieties are 5-6-membered or 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl, indanyl, decalinyl and indenyl.

The term "heterocyclyl" when used alone or in compound words includes any of monocyclic, polycyclic, fused or conjugated hydrocarbon residues, preferably $C_{3-20}$ (e.g. $C_{3-10}$ or $C_{3-8}$) wherein one or more carbon atoms are replaced by a heteroatom so as to provide a non-aromatic residue. Suitable heteroatoms include O, N, S, P and Se, particularly O, N and S. Where two or more carbon atoms are replaced, this may be by two or more of the same heteroatom or by different heteroatoms. The heterocyclyl group may be saturated or partially unsaturated, i.e. possess one or more double bonds. Particularly preferred heterocyclyl are 5-6 and 9-10 membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl, pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, pyranyl and dihydropyranyl.

The term "heteroaryl" includes any of monocyclic, polycyclic, fused or conjugated hydrocarbon residues, wherein one or more carbon atoms are replaced by a heteroatom so as to provide an aromatic residue. Preferred heteroaryl have 3-20 ring atoms, e.g. 3-10. Particularly preferred heteroaryl are 5-6 and 9-10 membered bicyclic ring systems.

Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, and furazanyl.

The term "acyl" either alone or in compound words denotes a group containing the agent C=O (and not being a carboxylic acid, ester or amide) Preferred acyl includes $C(O)-R^x$, wherein $R^x$ is hydrogen or an alkyl, alkenyl, alkynyl, aryl, heteroaryl, carbocyclyl, or heterocyclyl residue. Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenyihexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The $R^x$ residue may be optionally substituted as described herein.

The term "sulfoxide", either alone or in a compound word, refers to a group —$S(O)R^y$ wherein $R^y$ is selected from hydrogen, alkyl, alkenyl, alkynyl, aryl, heteroaryl, heterocyclyl, carbocyclyl, and aralkyl. Examples of preferred $R^y$ include $C_{1-20}$alkyl, phenyl and benzyl.

The term "sulfonyl", either alone or in a compound word, refers to a group —$S(O)_2-R^y$, wherein $R^y$ is selected from hydrogen, alkyl, alkenyl, alkynyl, aryl, heteroaryl, heterocyclyl, carbocyclyl and aralkyl. Examples of preferred $R^y$ include $C_{1-20}$alkyl, phenyl and benzyl.

The term "sulfonamide", either alone or in a compound word, refers to a group —$S(O)NR^yR^y$ wherein each $R^y$ is independently selected from hydrogen, alkyl, alkenyl, alkynyl, aryl, heteroaryl, heterocyclyl, carbocyclyl, and aralkyl. Examples of preferred $R^y$ include $C_{1-20}$alkyl, phenyl and benzyl. In a preferred embodiment at least one $R^y$ is hydrogen. In another form, both $R^y$ are hydrogen.

The term, "amino" is used here in its broadest sense as understood in the art and includes groups of the formula $NR^AR^B$ wherein $R^A$ and $R^B$ may be any independently selected from hydrogen, alkyl, alkenyl, alkynyl, aryl, carbocyclyl, heteroaryl, heterocyclyl, aralkyl, and acyl. $R^A$ and $R^B$, together with the nitrogen to which they are attached, may also form a monocyclic, or polycyclic ring system e.g.

a 3-10 membered ring, particularly, 5-6 and 9-10 membered systems. Examples of "amino" include $NH_2$, NHalkyl (e.g. $C_{1-20}$alkyl), NHaryl (e.g. NHphenyl), NHaralkyl (e.g. NHbenzyl), NHacyl (e.g. $NHC(O)C_{1-20}$alkyl, NHC(O)phenyl), Nalkylalkyl (wherein each alkyl, for example $C_{1-20}$, may be the same or different) and 5 or 6 membered rings, optionally containing one or more same or different heteroatoms (e.g. O, N and S).

The term "amido" is used here in its broadest sense as understood in the art and includes groups having the formula $C(O)NR^AR^B$, wherein $R^A$ and $R^B$ are as defined as above. Examples of amido include $C(O)NH_2$, C(O)NHalkyl (e.g. $C_{1-20}$alkyl), C(O)NHaryl (e.g. C(O)NHphenyl), C(O)NHaralkyl (e.g. C(O)NHbenzyl), C(O)NHacyl (e.g. $C(O)NHC(O)C_{1-20}$alkyl, C(O)NHC(O)phenyl), C(O)Nalkylalkyl (wherein each alkyl, for example $C_{1-20}$, may be the same or different) and 5 or 6 membered rings, optionally containing one or more same or different heteroatoms (e.g. O, N and S).

The term "carboxy ester" is used here in its broadest sense as understood in the art and includes groups having the formula $CO_2R^z$, wherein $R^z$ may be selected from groups including alkyl, alkenyl, alkynyl, aryl, carbocyclyl, heteroaryl, heterocyclyl, aralkyl, and acyl. Examples of carboxy ester include $CO_2C_{1-20}$alkyl, $CO_2$aryl (e.g., $CO_2$phenyl), $CO_2$aralkyl (e.g. $CO_2$ benzyl).

The term "heteroatom" or "hetero" as used herein in its broadest sense refers to any atom other than a carbon atom which may be a member of a cyclic organic group. Particular examples of heteroatoms include nitrogen, oxygen, sulfur, phosphorous, boron, silicon, selenium and tellurium, more particularly nitrogen, oxygen and sulfur.

The present invention will hereinafter be further described with reference to the following non-limiting examples.

EXAMPLES

General

Proton NMR spectra were obtained on Bruker AV400 and Bruker AV200 spectrometer, operating at 400 MHz and 200 MHz. All spectra were obtained at 23° C. unless specified. Chemical shifts are reported in parts per million (ppm) on the δ scale and relative to the chloroform peak at 7.26 ppm ($^1$H) or the TMS peak at 0.00 ppm ($^1$H). Oven dried glassware was used in all reactions carried out under an inert atmosphere (either dry nitrogen or argon). All starting materials and reagents were obtained commercially unless otherwise stated. Removal of solvents "under reduced pressure" refers to the process of bulk solvent removal by rotary evaporation (low vacuum pump) followed by application of high vacuum pump (oil pump) for a minimum of 30 min. Analytical thin layer chromatography (TLC) was performed on plastic-backed Merck Kieselgel KG60$F_{254}$ silica plates and visualised using short wave ultraviolet light, potassium permanganate or phosphomolybdate dip. Flash chromatography was performed using 230-400 mesh Merck Silica Gel 60 following established guidelines under positive pressure. Toluene was freshly distilled over sodium wire; triethylamine (TEA) was freshly distilled just prior to use. All other reagents and solvents were used as purchased, unless stated otherwise.

Procedure for the Synthesis of Cineole Diol from α-Pinene
(following L. A. Popova, V. I. Biba, V. M. Prishchepenko, S. V. Shavyrin and N. G. Kozlov., translated from *Zhurnal Obshch Khimii*, 1991, Vol. 62, No 7, 1639-1645)

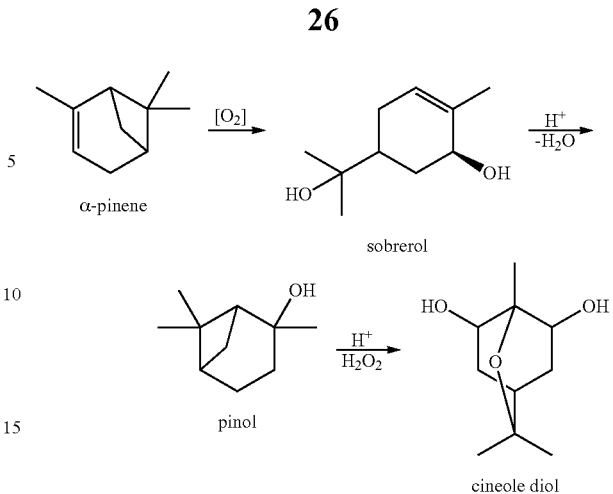

Synthesis of Sobrerol (p-menth-6-ene-2,8-diol)

Sobrerol is prepared according to the standard method by oxidation of α-pinene with oxygen from the air, giving the pure isomer with equatorial orientation of the substituent at the $C_4$ and pseudoaxial orientation of the hydroxyl group $C_2$. Commercially available sobrerol was sourced from Aldrich as 99% pure p-menth-6-ene-2,8-diol.

Synthesis of Pinol (6,8-epoxy-p-menth-1-ene)

The steam distillation of a flask loaded with sobrerol dissolved in 5% aqueous sulphuric acid gave the crude pinol. The pinol obtained after steam distillation was separated from the water in a separating funnel then dried, and distilled under vacuum by 183-184° C. to give pure product.

Synthesis of Cineole Diol (1,8-epoxy-p-menthane-2,6-diol)

Pinol is slowly added with vigorous stirring to a 1:3 ice cooled mixture of 30% aqueous $H_2O_2$ and 80% formic acid in such a way that the temperature did not exceed 40-45° C. The reaction was stirred at room temperature overnight and then neutralised with 10% aqueous KOH solution. Care was taken that the reaction temperature did not exceed 50° C. The reaction mixture was allowed to cool to room temperature before the organics were extracted with diethyl ether. The extract was dried, filtered and the solvent removed to yield the crude product. Re-crystallisation from hot hexane gave fine white crystals of cineole diol in good yield (mp. 120-125° C.). The $^1$H and $^{13}$C NMR spectra matched the literature. The total synthesis of cineole diol was repeated several times on 100 g scale.

$^1$H-NMR (CDCl$_3$, 400 MHz): δ[ppm]=3.82-3.79 (m, 2H), 3.42 (s, 2H), 2.6-2.5 (m, 2H), 1.64 (s, 1H), 1.50, 1.47 (d, 2H), 1.31 (s, 3H), 1.18 (s, 6H).

Procedure for the synthesis of 2,2'-((1,3,3-trimethyl-2-oxabicyclo[2.2.2]octane-6,7-diyl)bis(oxy) diethanol from cineole diol

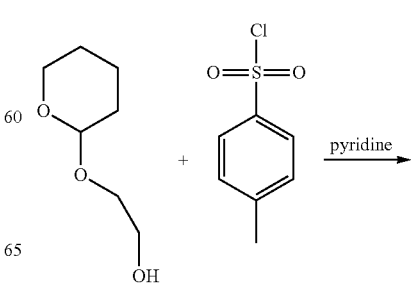

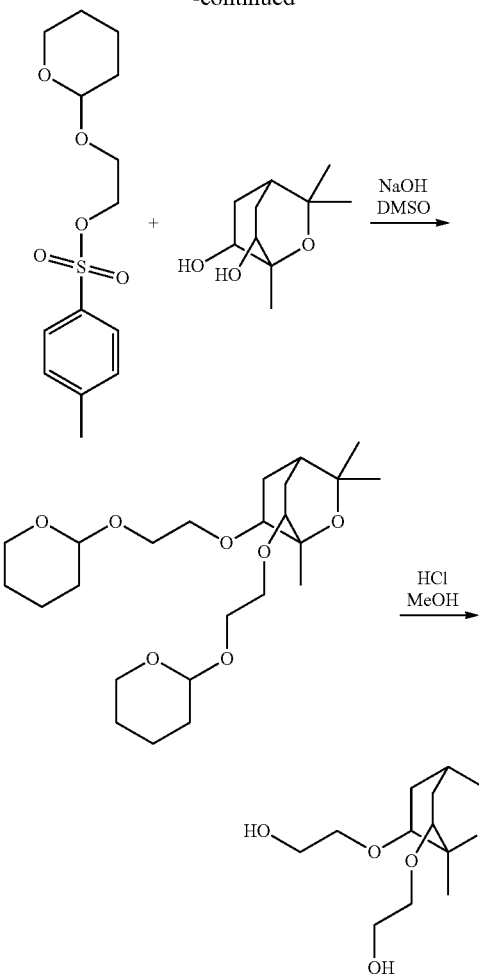

1) Synthesis of 2-((tetrahydro-2H-pyran-2-yl)oxy)ethyl 4-methylbenzenesulfonate

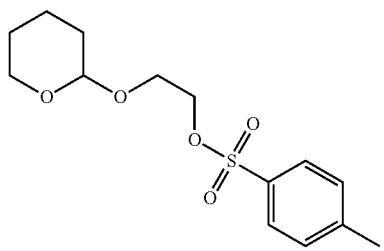 [SMILES: Cc1ccc(S(=O)(=O)OCCOC2CCCCO2)cc1]

E. Weber, Liebigs Ann. Chem, 1983, pp 772

2-((tetrahydro-2H-pyran-2-yl)oxy)ethanol (27.22 g, 186.21 mmol) was dissolved in 120 ml pyridine and the mixture was cooled to −10_° C. 4-methylbenzene-1-sulfonyl chloride (37.28 g, 195.50 mmol) was added and the mixture was allowed to stir for 2 h at −10° C. After stirring for 2 h the reaction mixture was poured over ice water (150 ml). The water/reaction mixture was extracted with dichloroethane (4×150 ml), The combined organic layers were extracted with 10% aqueous $CuSO_4$ solution (5×150 ml) until no colour change (purple to blue) was observed. After that the combined organic layers were extracted with saturated aqueous $NH_4Cl$ solution (3×150 ml), saturated aqueous NaCl solution (1×150 ml), dried over $MgSO_4$, filtered and the solvent removed under reduced pressure yielding 40.46 g (134.70 mmol, 72%). The crude product was used in the next step without further purification.

$^1$H-NMR ($CDCl_3$, 200 MHz): δ[ppm]=7.81, 7.34 (dd, 4H, J=8.0 Hz), 4.62-4.49 (m, 1H), 4.17 (t, 2H, J=5.0), 3.95-3.35 (m, 4H), 2.45 (s, 3H), 1.91-1.38 (m, 6H)

2) Synthesis of 1,3,3-trimethyl-6,7-bis(2-((tetrahydro-2H-pyran-2-yl)oxy)ethoxy)-2-oxabicyclo[2.2.2]octane

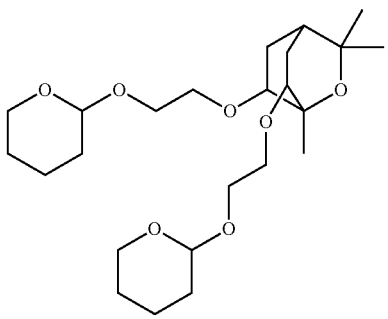 [SMILES: CC1(C)OC2(C)C(OCCOC3CCCCO3)CC1CC2OCCOC1CCCCO1]

P. R. Ashton et al, *Eur. J. Org. Chem.* 1999, 995-1005

A suspension of finely ground NaOH (6.6 g, 165 mmol) in DMSO (100 ml) was stirred mechanically for 15 min at 50_° C. Cineol diol (3.91 g, 21 mmol) was added to the mixture and stirring and heating were maintained for 1 h. A solution of 2-((tetrahydro-2H-pyran-2-yl)oxy)ethyl 4-methylbenzenesulfonate (18.5 g, 62 mmol) in DMSO (30 ml) was added and the resulting mixture was heated for 18 h at 80° C. with stirring. After cooling down to ambient temperature, the solvent was removed under reduced pressure by trap to trap distillation and the solid residue was treated with a 1:1 (v/v) mixture of $CHCl_3/H_2O$ (800 ml). The organic layer was washed with $H_2O$ and dried ($MgSO_4$). The solvent was removed under reduced pressure and the residue was purified by column chromatography ($SiO_2$/EtOAc) to yield 1,3,3-trimethyl-6,7-bis(2-((tetrahydro-2H-pyran-2-yl)oxy)ethoxy)-2-oxabicyclo[2.2.2]octane (4.8 g, 10 mmol).

$^1$H-NMR ($CDCl_3$, 400 MHz): δ[ppm]=4.71-4.59 (m, 2H), 3.95-3.35 (m, 12H), 2.55-2.48 (m, 2H), 1.91-1.39 (m, 17 H), 1.34 (s, 3H), 1.22 (s, 6H)

3) Synthesis of 2,2'-((1,3,3-trimethyl-2-oxabicyclo[2.2.2]octane-6,7-diyl)bis(oxy))diethanol

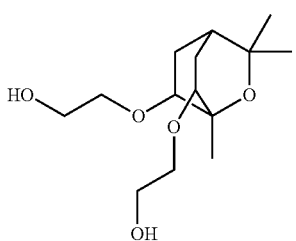 [SMILES: CC1(C)OC2(C)C(OCCO)CC1CC2OCCO]

Concentrated aqueous HCl) 0.5 ml) was added to a solution of 1,3,3-trimethyl-6,7-bis(2-((tetrahydro-2H-pyran-2-yl)oxy)ethoxy)-2-oxabicyclo[2.2.2]octane .8 g, 10 mmol) in methanol (30 ml). The solution was stirred over night at ambient temperature after which time no traces of starting material were present by TLC ($SiO_2$/$CHCl_3$/MeOH, 100:1, (v/v)). The solution was filtered, concentrated and the residue was dissolved in $CHCl_3$ and dried ($K_2CO_3$) to yield (2.46 g. 9 mmol, 90%) as a yellow oil.

$^1$H-NMR ($CDCl_3$, 200 MHz): δ[ppm]=3.85-3.35 (m, 10H), 2.55-2.48 (m, 2H), 1.69-1.61 (m, 1H), 1.55-1.43 (m, 2H), 1.31 (s, 3H), 1.18 (s, 6H)

Procedure for the synthesis of 2,2'-((1,3,3-trimethyl-2-oxabicyclo[2.2.2]octane-6,7-diyl)bis(oxy)) diacetic acid from 2,2'-((1,3,3-trimethyl-2-oxabicyclo[2.2.2]octane-6,7-diyl)bis(oxy))diethanol

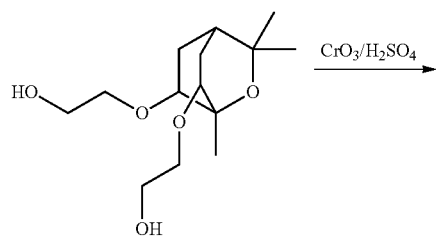

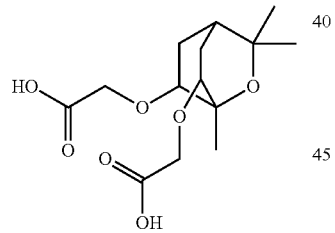

To a solution of 2,2'4(1,3 ,3-trimethyl-2-oxabicyclo[2.2.2]octane-6,7-diyl)bis(oxy))diethanol (0.5 g, 1.8 mmol) in acetone (10 ml) was added 2 ml of Jones Reagent (The Jones Reagent is a solution of chromium trioxide in diluted sulfuric acid that can be used safely for oxidations of organic substrates in acetone). The reaction mixture was allowed to stir at ambient temperature for 2 h. After that 5 ml of 2-propanol was added. The chromium salts were removed through filtration and the organic solvents were removed under reduced pressure. The crude product was dissolved in ethyl acetate (10 ml), extracted with 0.01M HCl solution (3×10ml) and dried over $MgSO_4$. The organic solvent was removed under reduced pressure and the product (0.52 g, 1.7 mmol, 95%) can be used in the subsequent step without further purification)

$^1$H-NMR ($CDCl_3$, 200 MHz): δ[ppm]=6.11-5.35 (br, 2H), 4.32-3.98 (m, 4H), 3.87-3.51 (m, 2H), 2.86-1.97 (m, 3H), 1.73-1.43 (m, 2H), 1.41-1.03 (m, 9H)

Polymer Methods

Polyesters

Method A: Generic Procedure for the polymerisation of cineole diol with TPA

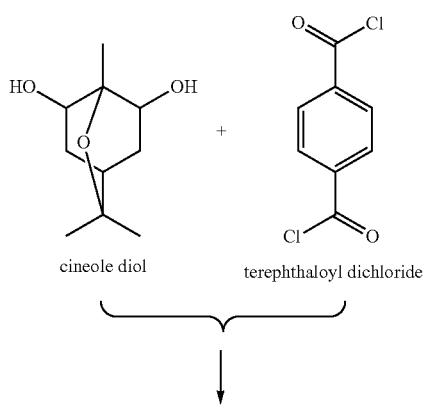

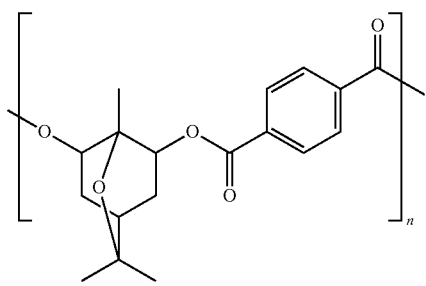

A flame-dried 50 ml round bottomed flask, equipped with stirring bar, reflux condenser with serum cap, argon inlet (through serum cap), was charged with 100 mL of dry chloroform, 5.0 g (0.024 mol) of terephthaloyl chloride, 4.86 g (0.024 mol) of cineole diol (this amount changed depending on the desired composition) and 5.09 g (0.084 mol) of freshly distilled triethylamine (TEA). The resulting solution was brought to reflux and left to react overnight. The mixture was extracted with chloroform and washed with water three times. The organic factions were collected, dried and the solvent was removed in vacuo to yield the product. This product was then dried in a vacuum oven overnight. Samples for $^1$H and $^{13}$C NMR were made up using minimal NMR grade trifluoroacetic acid to first dissolve the polymer then making up the rest of the solvent with $CDCl_3$.

Method B: Generic Procedure for the polymerisation of cineole diol, TPA and propane-1,3-diol

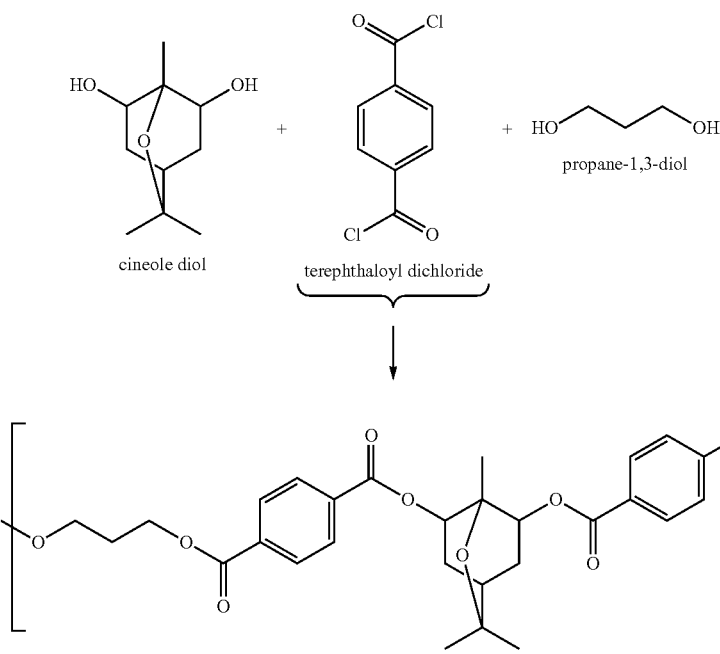

A flame-dried 50 mL round bottomed flask, equipped with stirring bar, reflux condenser with serum cap, argon inlet (through serum cap), was charged with 100 mL of dry chloroform, 5.0 g (0.024 mol) of terephthaloyl chloride, 1.68 g (0.022 mol) of 1,3-propanediol, 0.486 g (0.0024 mol) of cincole diol (this amount changed depending on the desired composition) and 5.09 g (0.084 mol) of freshly distilled triethylamine (TEA). The resulting solution was brought to reflux and left to react overnight. The mixture was extracted with chloroform and washed with water three times. The organic factions were collected, dried and the solvent was removed in vacuo to yield the product. This product was then dried in a vacuum oven overnight. Samples for $^1$H and $^{13}$C NMR were made up using minimal NMR grade trifluoroacetic acid to first dissolve the polymer then making up the rest of the solvent with $CDCl_3$.

Method C: Generic Procedure for the polymerisation of Cineole diol, TPA and ethylene glycol

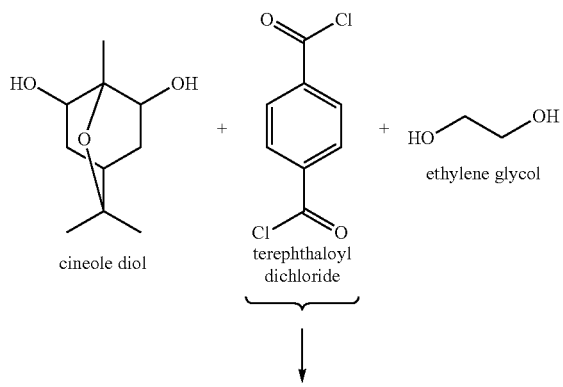

-continued

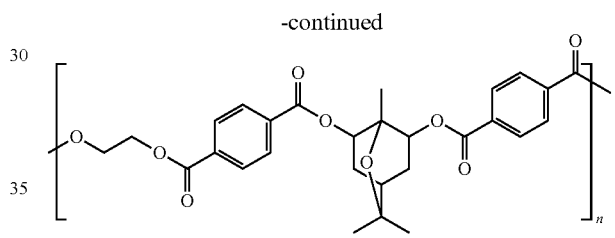

A flame-dried 50 mL round bottomed flask, equipped with stirring bar, reflux condenser with serum cap, argon inlet (through serum cap), was charged with 100 mL of dry chloroform, 5.0 g (0.024 mol) of terephthaloyl chloride, 1.36 g (0.022 mol) of ethylene glycol, 0.486 g (0.0024 mol) of cineole diol (this amount changed depending on the desired composition) and 5.09 g (0.084 mol) of freshly distilled tricthylaminc (TEA). The resulting solution was brought to reflux and left to react overnight. The mixture was extracted with chloroform and washed with water three times. The organic factions were collected, dried and the solvent was removed in vacuo to yield the product. This product was then dried in a vacuum oven overnight. Samples for $^1$H and $^{13}$C NMR were made up using minimal NMR grade trifluoroacetic acid to first dissolve the polymer then making up the rest of the solvent with $CDCl_3$.

Method D: Generic Procedure for the polymerisation of Cineole diol and succinyl dichloride

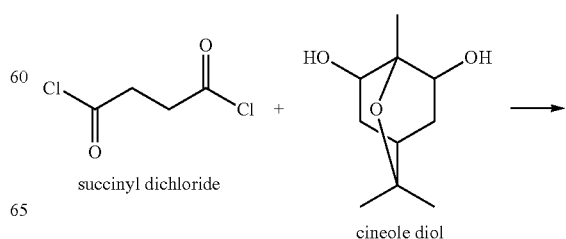

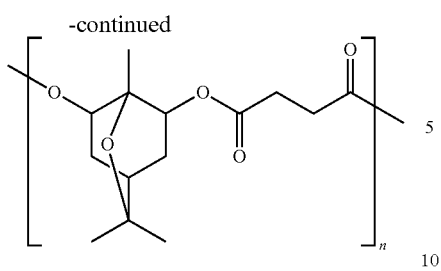

A flame-dried 50 mL round bottomed flask, equipped with stirring bar, reflux condenser with serum cap, argon inlet (through serum cap), was charged with 10 mL of dry chloroform, 0.41 g (2.6 mmol) of succinyl dichloride, 0.5 g (2.6 mmol) of cineole diol and 2.6 g (2.6 mmol) of freshly distilled triethylamine (TEA). The resulting solution was brought to reflux and left to react overnight. The mixture was extracted with chloroform and washed with water three times. The organic factions were collected, dried and the solvent was removed in vacuo to yield the product. This product was then dried in a vacuum oven overnight. Samples for $^1H$ and $^{13}C$ NMR were made up using minimal NMR grade trifluoroacetic acid to first dissolve the polymer then making up the rest of the solvent with $CDCl_3$.

Method E: Generic Procedure for the polymerisation of Cineole diol and adipoly dichloride

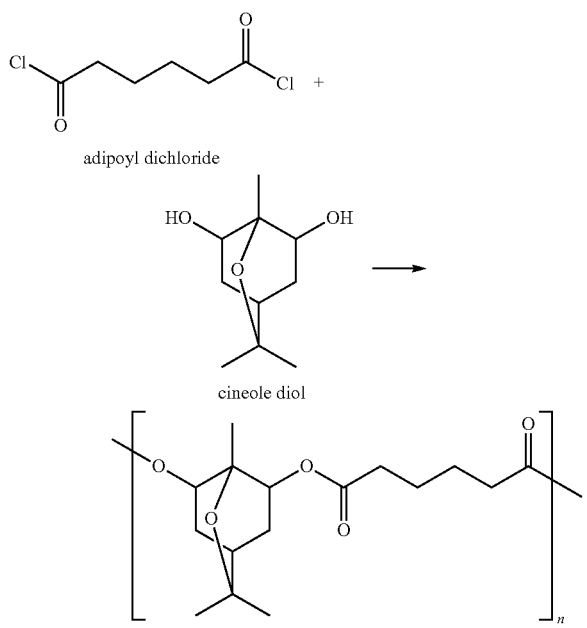

A flame-dried 150 mL round bottomed flask, equipped with stirring bar, reflux condenser with serum cap, argon inlet (through serum cap), was charged with 50 mL of dry dichloromethane (DCM) containing 1.83 g (10.0 mmol) of cineole diol. 1.83 g (10.0 mmol) of adipoly dichloride was added slowly via glass syringe. 2mmol of Pyridine was added over 15 minutes and 2.6 g (2.6 mmol) and the mixture was allowed to stir overnight.

The pryridine salt crystals were filtered off and the DCM was removed by rotovap. The resulting solution was brought to reflux and left to react overnight. . Samples for $^1H$ and were made up using minimal NMR grade $CDCl_3$.

Polyurethanes
Method F: Generic Procedure for the polymerisation of cineole diol and toluene diisocyanates

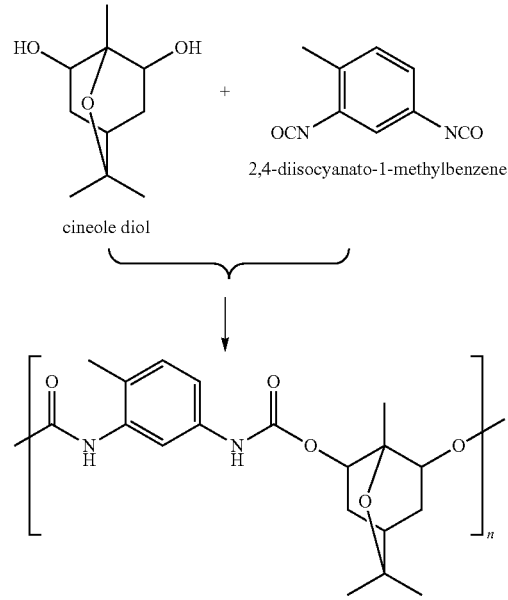

An oven dried 50 mL flask was charged with vacuum oven dried 1 g (5.3 mmol) of cineole diol. The flask was then placed in an oven at 150° C. until the cineole diol had melted. 2 drops of the catalyst dibutyltindilaurate was added. The mixture was then stirred rapidly with a spatula while 0.935 g (5.3 mmol) of 2,4-diisocyanato-1-methylbenzene was added. The mixture solidified within two minutes giving the product. The product was returned to the oven at 90° C. and left overnight. Samples for $^1H$ and $^{13}C$ NMR were made up using minimal NMR grade trifluoroacetic acid to first dissolve the polymer then making up the rest of the solvent with $CDCl_3$.

Method G: Generic Procedure for the polymerisation of cineole diol and MDI

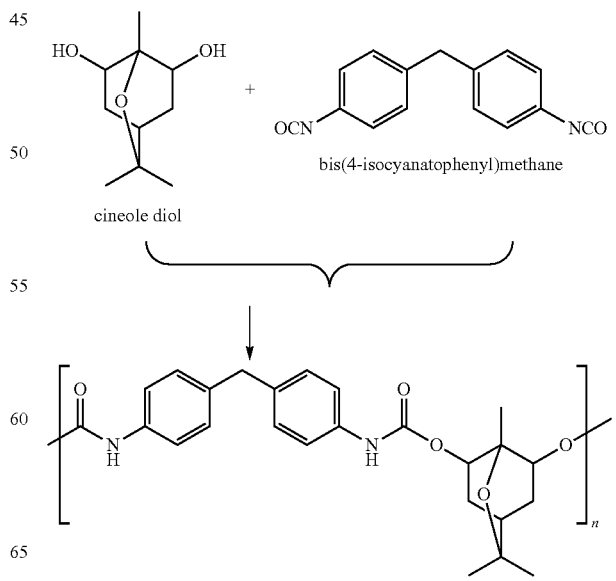

An oven dried 50 mL flask was charged with vacuum oven dried 2 g (10.7 mmol) of cineole diol. The flask was then placed in an oven at 150° C. until the cineole diol had melted. 2 drops of the catalysts dibutyltindilaurate was added. The mixture was then stirred rapidly with a spatula while 2.68 g (10.7 mmol) of bis(4-isocyanatophenyl)methane (MDI) was added. The product was returned to the oven at 90° C. and left overnight. Samples for $^1$H were made up using minimal NMR grade deuterated DMSO added. The mixture was then stirred rapidly with a spatula while 1.8 g (10.7 mmol) of 1,6-diisocyanatohexane was added. The mixture solidified within two minutes giving the product. The product was returned to the oven at 90° C. and left overnight. Samples for $^1$H were made up using minimal NMR grade in deuterated DMSO Method I: Generic Procedure for the polymerisation of EG-CD and HDI

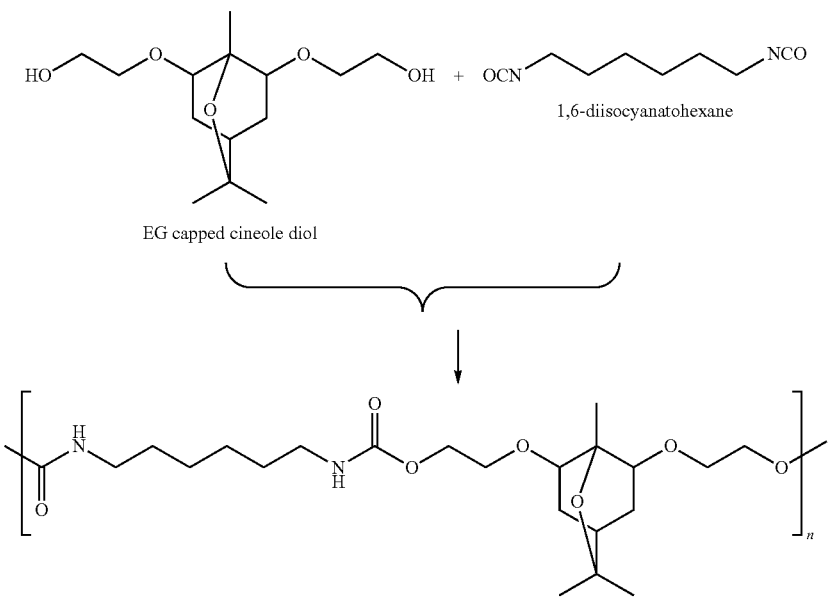

EG capped cineole diol 1,6-diisocyanatohexane

Method H: Generic Procedure for the polymerisation of cineole diol and HDI

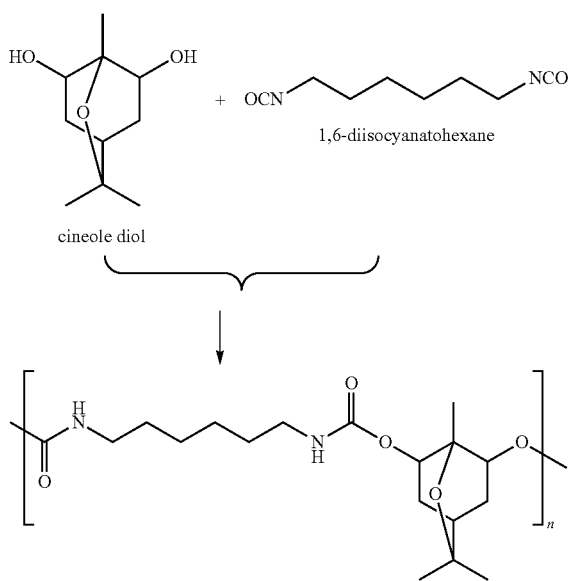

cineole diol 1,6-diisocyanatohexane

An oven dried 50 mL flask was charged with vacuum oven dried 2 g (10.7 mmol) of cineole diol. The flask was then placed in an oven at 150° C. until the cineole diol had melted. 2 drops of the catalysts dibutyltindilaurate was An oven dried 50 mL flask was charged with vacuum oven dried 2 g (7.28 mmol) of EG capped cineole diol. The flask was then placed in an oven at 150° C. until the cineole diol had melted. 2 drops of the catalysts dibutyltindilaurate was added. The mixture was then stirred rapidly with a spatula while 1.22 g (7.28 mmol) of 1,6-diisocyanatohexane was added. The mixture solidified within two minutes giving the product. The product was returned to the oven at 90° C. and left overnight. Samples for $^1$H were made up in deuterated DMSO Transesterifcation Method J: Generic procedure for the reaction of CD with PET

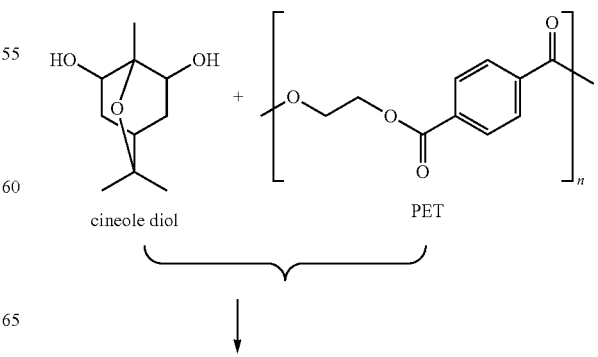

cineole diol

PET

-continued

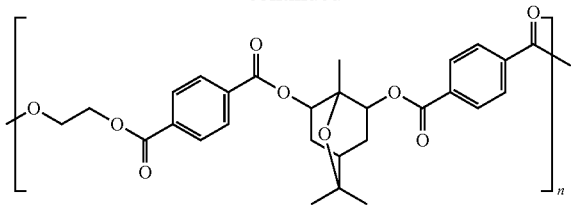

A 25 mL glass ampoule was dried in an oven. The ampoule was fitted with a magnetic stirrer was charged with vacuum oven dried 0.323 g (1.73 mmol) cineole diol and 3.00 g PET (Dianite IV=1.2 dg/L), dried to <25 ppm water. The ampoule was then placed under vacuum and stirred on a magnetic stirrer for 3 hours. The ampoule was then sealed while under vacuum using a gas torch. The ampoule was then heated to 280° C. in an open 100mL Parr reactor filled with sand as a heat transfer medium. The ampoule was heated and agitated until the PET and CD was molten. Heating was continued until no more of the cineole diol was found to sublime at the top of the ampoule. The ampoule was then cooled and opened and the contents were analysed by NMR and GPC.

Method K: Generic Procedure for the reaction of EG-CD with PET

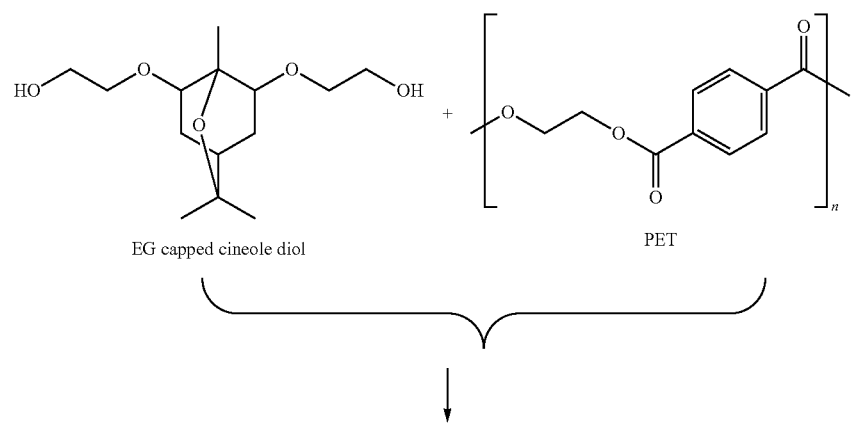

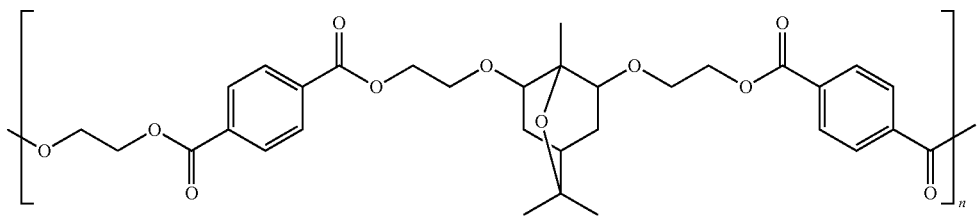

A 25 mL glass ampoule was dried in an oven. The ampoule was fitted with a magnetic stirrer was charged with vacuum oven dried 0.238 g (0.87 mmol) cineole diol and 1.5 g PET (Dianite IV=1.2 dg/L), dried to <25 ppm water. The ampoule was then placed under vacuum and stirred on a magnetic stirrer for 3 hours. The ampoule was then sealed while under vacuum using a gas torch. The ampoule was then heated to 280° C. in an open 100 mL Parr reactor filled with sand as a heat transfer medium. The ampoule was heated and agitated until the PET and CD was molten. Heating was continued until no more of the CD was found to sublime at the top of the ampoule. The ampoule was then cooled and opened and the contents were analysed by NMR and GPC.

Polyamides
Method L: Generic Procedure for the reaction of HAA-CD with HDI to form a polyamide

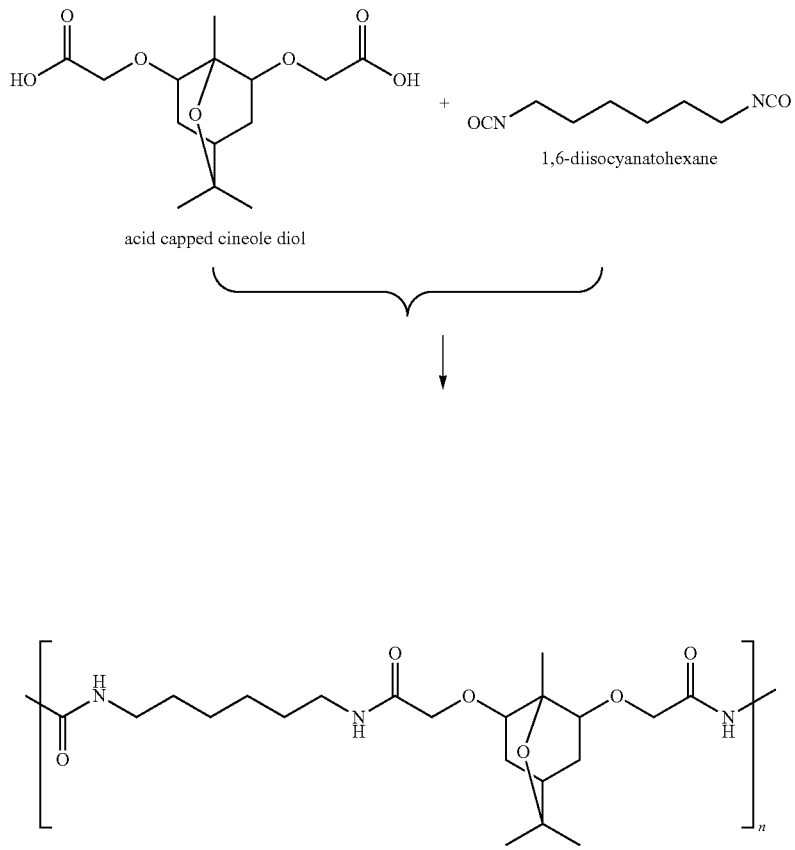

An oven dried 50 mL flask was charged with vacuum oven dried 2 g (6.62 mmol) of Acid capped cineole diol (A-CD). The flask was then placed in an oven at 150° C. until the cineole diol had melted. 2 drops of the catalysts dibutyltindilaurate was added. The mixture was then stirred rapidly with a spatula while 1.11 g (6.62 mmol) of 1,6-diisocyanatohexane was added. The mixture was found to foam indicating the elimination of carbon dioxide to produce the amide. The product was returned to the oven at 90° C. and left overnight. Samples for $^1$H were made up in deuterated DMSO Characterisation of Polymers Polymer Samples were Characterised by a Number of Techniques as Described below:

NMR—Nuclear Magnetic Resonance

Proton NMR spectra were obtained on Bruker AV400 and Bruker AV200 spectrometer, operating at 400 MHz and 200 MHz. All spectra were obtained at 23° C. unless specified.

Chemical shifts are reported in parts per million (ppm) on the δ scale and relative to the chloroform peak at 7.26 ppm ($^1$H) or the TMS peak at 0.00 ppm ($^1$H).

Thermal Analysis:

DSC (Differential Scanning calorimetry) was undertaken on the polymers produced using the method described above. Samples were weighed into aluminium pans and the pans placed in a round bottom flask and dried under vacuum at room temperature overnight. Lids were crimped on the DSC pans and they were then weight to determine the dry weight.

DSC scans were conducted using a Mettler Star SW 9.00 DSC. Thermal scans were conducted under a nitrogen gas purge using the following method. The pans were heated from 30° C. to 270° C. at 50° C./min, held at 270° C. for 1min and then cooled at 50° C./min to −20° C. (to get sample contact with the pan), the pans were held at −20° C. for 5mins., the pans were then heated at 10° C./min to 270° C.

Intrinsic Viscosity (IV):

The intrinsic viscosity of the modified PET was measured using ASTM Method D4603-03: Determining the intrinsic viscosity of PET by Glass Capillary Viscometer. The solvent mixture used was a 1:4 mixture of TFA (triflouro acetic acid) and DCM (dichloro methane). The IV was measured using a type 1 Ubedeholle Viscometer. The IV was measured using a thermostat controlled water bath at 25° C.

In Table 1 below, the following abbreviations were used: terephthalic acid (TPA), cineole diol (CD) ethylene glycol capped cineole diol (EG-CD), Carboxy ethyl capped-cineole diol (CE-EG), ethylene glycol (E.G.), 1,3-propane glycol (PG), succinic acid (SA), succinoyl chloride (SC), adipoly chloride (AC), 2,4-diisocyanato-1-methylbenzene (TDI), bis (4-isocyanatophenyl)methane (MDI), 1,6-diisocyanato-hexane (HDI); pyromellitic dianhydride (PMDA).

Despite the abbreviations used it will be understood that a copolymer of terephthalic acid and the cyclic compound of Formula (I) where X and Y are H may be formed from the polymerisation of terephthalic acid dichloride and the cyclic diol. Likewise succinyl acid dichloride may be used to form a succinic acid copolymer.

TABLE 1

| Example | Polymer | Modifier (mole % Cincole diol) | Method | $^1$H NMR |
|---|---|---|---|---|
| 1 | TPA, CD (polyester) | 50 | A | 8.17 (m, 4H), 5.1 (s, 1H), 3.92 (s, 1H), 2.84-2.73 (m, 2H), 1.96 (s, 1H), 1.77 (s, 1H), 1.53 (m, 3H), 1.31 (m, 9H). |
| 2* | TPA, PG (polyester) | 0 | A | 8.11 (s, 4H), 4.62 (s, 4H), 2.38 (s, 2H). |
| 3 | TPA, CD, PG (polyester) | 5 | B | 8.12 (m, 4H), 5.20 (s, 5% of 1H), 4.62 (s, 4H), 4.20 (s, 5% of 1H), 2.92 (m, 5% of 2H), 2.38 (s, 2H), 1.89 (s, 5% of 1H), 1.63 (m, 5% of 3H), 1.41 (s, 5% of 9H). |
| 4 | TPA, CD, PG (polyester) | 10 | B | 8.10 (m, 4H), 5.20 (s, 10% of 1H), 4.62 (s, 90% of 4H), 4.20 (s, 10% of 1H), 2.92 (m, 10% of 2H), 2.38 (s, 90% of 2H), 1.89 (s, 10% of 1H), 1.63 (m, 10% of 3H), 1.41 (s, 10% of 9H). |
| 5 | TPA, CD, PG (polyester) | 20 | B | 8.06 (m, 4H), 5.20 (s, 20% of 1H), 4.53 (s, 80% of 4H), 4.20 (s, 20% of 1H), 2.92 (m, 20% of 2H), 2.38 (s, 80% of 2H), 1.89 (s, 20% of 1H), 1.63 (m, 20% of 3H), 1.41 (s, 20% of 9H). |
| 6* | TPA, E.G. (polyester) | 0 | C | 8.14 (s, 4H), 4.80 (s, 4H) |
| 7 | TPA, CD, E.G. (polyester) | 5 | C | 8.12 (m, 4H), 5.20 (s, 5% of 1H), 4.62 (s, 95% of 4H), 4.20 (s, 5% of 1H), 2.92 (m, 5% of 2H), 2.38 (s, 95% of 2H), 1.89 (s, 5% of 1H), 1.63 (m, 5% of 3H), 1.41 (s, 5% of 9H). |
| 8 | TPA, CD, E.G. (polyester) | 10 | C | 8.12 (m, 4H), 5.20 (s, 10% of 1H), 4.77 (s, 90% of 4H), 4.20 (s, 10% of 1H), 2.92 (m, 10% of 2H), 2.38 (s, 90% of 2H), 1.89 (s, 10% of 1H), 1.63 (m, 10% of 3H), 1.41 (s, 10% of 9H). |
| 9 | TPA, CD, E.G. (polyester) | 20 | C | 8.08 (m, 4H), 5.16 (s, 20% of 1H), 4.67 (s, 80% of 4H), 4.20 (s, 20% of 1H), 2.87 (m, 20% of 2H), 2.38 (s, 80% of 2H), 1.89 (s, 20% of 1H), 1.63 (m, 20% of 3H), 1.35 (s, 20% of 9H). |
| 10 | CD, SC (polyester) | 50 | D | 4.88 (s, 2H), 4.03-3.83 (m, 2H), 2.70 (m, 6H), 2.35 (s, 1H), 1.71-1.09 (m, 12H) |
| 11 | CD, AC (polyester) | 50 | E | 4.89-4.79 (m, 2H), 2.76-2.61 (m, 2H), 2.42-2.28 (m, 4H), 1.88-1.64 (m, 6H), 1.52-1.02 (m, 12H) |
| 12 | CD, TDI (polyurethane) | 50 | F | 7.09 (m, 3H), 4.90 (m, 2H), 3.84 (s, 1H), 2.72 (s, 2H), 2.27 (m, 4H), 1.72-1.46 (m, 4H), 1.29 (m, 14H) |
| 13 | CD, MDI (polyurethane) | 50 | G | 9.50 (s), 8.56 (s), 7.99 (s), 750-730 (m), 7.24-7.05 (m), 4.76-4.66 (m), 4.11-3.58 (m), 2.93 (s), 2.77 (s), 2.25-2.29 (m), 1.74-1.67 (m), 1.57-1.00 (m) |
| 14 | CD, HDI (polyurethane) | 50 | H | 4.74 (s, 2H), 3.11 (s, 4H), 2.63 (s, 2H), 1.77-1.69 (m, 2H), 1.25 (m, 18H) |
| 15 | EG-CD, HDI Poly(ether-urethane) | 50 | I | 5.72-4.52 (br, 2H), 4.37-4.02 (m, 4H), 3.92-3.37 (m, 6H), 3.27-3.01 (m, 4H), 2.62-2.28 (m, 2H), 1.91-1.01 (m, 20H) |
| 16 | CE-HDI (Polyamide) | 50 | L | 6.99-6.78 (br), 6.42-6.23 (br), 4.34-3.45 (m), 3.37-3.04 (m), 2.84-2.04 (m), 1.84-1.02 (m) |
| 17 | CD-PET (Polyester) | 5 | J | 8.31-8.01 (m), 4.71 (s), 3.97-3.63 (m), 2.76-2.07 (m), 1.83-1.11 (m) |
| 18 | CD-PET (Polyester) | 10 | J | 8.31-8.01 (m), 7.41-7.13 (m), 4.71 (s), 4.51 (s), 4.01-3.59 (m), 2.79-2.17 (m), 1.89-1.01 (m) |
| 19 | CD-PET (Polyester) | 15 | J | 8.31-8.01 (m), 7.40-7.15 (m), 4.72 (s), 4.50 (s), 4.03-3.61 (m), 2.81-2.17 (m), 1.89-1.09 (m) |
| 20 | CD-PET (Polyester) | 20 | J | 8.32-8.06 (m), 7.39-7.13 (m), 4.71 (s), 4.53 (s), 4.02-3.58 (m), 2.77-2.11 (m), 1.81-1.07 (m) |
| 21 | CD-PET PDMA (Polyester) | 10 | J | 8.32-8.06 (m), 7.43-6.98 (m), 4.73 (s), 4.51 (s), 3.66-2.01 (br), 1.71-1.21 (m) |
| 22 | CD-PET PDMA (Polyester) | 20 | J | 8.31-8.05 (m), 7.49-6.91 (m), 6.71-6.61 (m), 4.73 (s), 4.51 (s), 3.16-1.51 (m), 1.31-1.21 (m) |
| 23 | CE-CD PET (Polyester) | 10 | K | 8.31-8.05 (m), 4.73 (s), 4.51 (s), 3.99-3.51 (m), 2.53-2.48 (m), 1.81-1.15 (m) |

*Comparative example

Thermal Analysis

Thermal analysis, by DSC, of the polymer from Example 1 (Cineole diol-TPA) has shown that the polymer has a glass transition temperature of approximately 150° C. The Cineole diol-TPA polymer was found not to melt at 270° C. It is expected that if the molecular weight of the CD-TPA polymer was increased by polycondensation or coupling methods that the Tg would also be increased.

Intrinsic Viscosity

The following IV's were measured for the Examples
Example 1:IV=0.055 dL/g
Example 11:IV=0.037 dL/g Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Many modifications will be apparent to those skilled in the art without departing from the scope of the present invention.

The invention claimed is:

1. A compound for use in preparation of polymer, the compound being selected from:

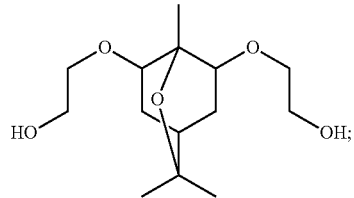

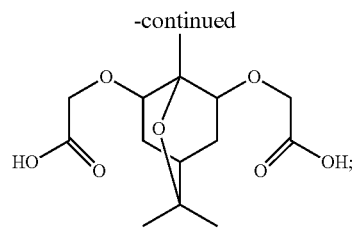

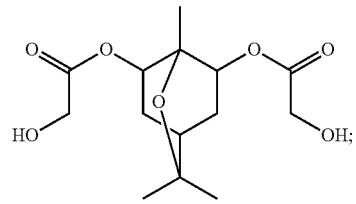

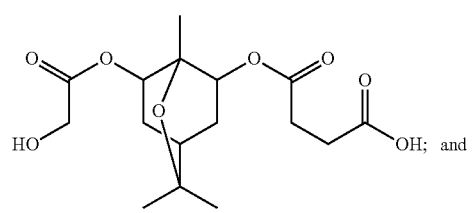

and

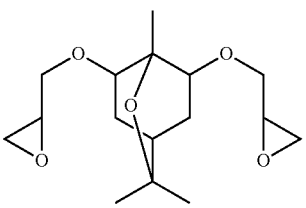

* * * * *